(12) United States Patent
Zhang

(10) Patent No.: US 9,206,192 B2
(45) Date of Patent: Dec. 8, 2015

(54) TROLOX DERIVATIVE-MODIFIED FAT-SOLUBLE ANTI-CANCER PHARMACEUTICAL COMPOUNDS, PREPARATIONS, PREPARING METHODS AND USE THEREOF

(71) Applicant: CHIA TAI TIANQING PHARMACEUTICAL GROUP CO., LTD, Lianyungang (CN)

(72) Inventor: Yuehua Zhang, Nanjing (CN)

(73) Assignee: Jiangsu Chiatei Tianqing Pharmaceutical Co., LTd, Jiangsu (CN)

( * ) Notice: Subject to any disclaimer, the term of this patent is extended or adjusted under 35 U.S.C. 154(b) by 0 days.

(21) Appl. No.: 14/357,560

(22) PCT Filed: Oct. 18, 2012

(86) PCT No.: PCT/CN2012/083161
§ 371 (c)(1),
(2) Date: May 9, 2014

(87) PCT Pub. No.: WO2013/067882
PCT Pub. Date: May 16, 2013

(65) Prior Publication Data
US 2014/0343088 A1 Nov. 20, 2014

(30) Foreign Application Priority Data

Nov. 11, 2011 (CN) .......................... 2011 1 0355747

(51) Int. Cl.
| | | |
|---|---|---|
| *C07D 498/00* | (2006.01) | |
| *C07D 491/22* | (2006.01) | |
| *C07F 9/655* | (2006.01) | |
| *C07F 9/6561* | (2006.01) | |
| *A61K 9/107* | (2006.01) | |
| *A61K 47/48* | (2006.01) | |
| *A61K 47/10* | (2006.01) | |
| *A61K 47/44* | (2006.01) | |

(52) U.S. Cl.
CPC .............. *C07D 491/22* (2013.01); *A61K 9/107* (2013.01); *A61K 9/1075* (2013.01); *A61K 47/48107* (2013.01); *C07F 9/6561* (2013.01); *C07F 9/65522* (2013.01); *A61K 47/10* (2013.01); *A61K 47/44* (2013.01)

(58) Field of Classification Search
CPC ..................................................... C07D 491/22
USPC .......................................................... 546/48
See application file for complete search history.

(56) References Cited

U.S. PATENT DOCUMENTS

2008/0045559 A1* 2/2008 Zhang et al. .................. 514/283

FOREIGN PATENT DOCUMENTS

| CN | 1875022 A | 12/2006 |
|---|---|---|
| WO | 2010/060098 A1 | 5/2010 |

OTHER PUBLICATIONS

Venkatesh et al., J. Pharm. Sci. 89, 145-54 (2000).*
International Search Report for PCT/CN2012/083161 mailed on Jan. 24, 2013.

* cited by examiner

*Primary Examiner* — Nizal Chandrakumar
(74) *Attorney, Agent, or Firm* — Kilpatrick Townsend & Stockton LLP

(57) ABSTRACT

Disclosed is a trolox derivative-modified fat-soluble anti-cancer pharmaceutical compound having a structure as represented by formula I or II. An active moiety of the anti-cancer pharmaceutical compound, camptothecin or a camptothecin derivative, is covalently bonded to a lipophilic moiety, a trolox ester or a trolox amide, by a linking group to form the fat-soluble anti-cancer pharmaceutical compound. Also disclosed are a preparation, preparing method and use of the pharmaceutical compound.

7 Claims, 6 Drawing Sheets

TROLOX DERIVATIVE-MODIFIED FAT-SOLUBLE ANTI-CANCER PHARMACEUTICAL COMPOUNDS, PREPARATIONS, PREPARING METHODS AND USE THEREOF

TECHNICAL FIELD

The present invention relates to novel anti-cancer pharmaceutical compounds, preparing methods and uses thereof, and in particular, to trolox derivative-modified fat-soluble anti-cancer pharmaceutical compounds, preparations comprising the same, methods for preparing the same, and a use of the same as an anti-cancer medicament.

BACKGROUND

The fact that many compounds having anti-cancer activity are either insoluble or insufficiently stable in water and other biocompatible solvents has become a burden in drug development, and usually delays the drug development. It is estimated that up to 40% of screened pharmaceutical candidate compounds having potential values are denied the entry into the formulation research and development stage due to their poor water-solubility. In addition, 30% of existing drugs are insoluble. Several technologies currently under research and development are intended to solve the problem related to poor solubility of pharmaceutical compounds. Such technologies include a complexant technology for increasing solubility, a nanoparticle technology, a microemulsion technology, a formulation technology for increasing solubility, a fat-soluble or water-soluble prodrug technology, and a new polymer carrier technology and the like.

Camptothecin (20(s)-camptothecin, formula 1, 1) and its derivatives have good anti-tumor activity, and belong to a class of important DNA topoisomerase I (Top I) inhibitors. They can bind to Top I-DNA cleavable complexes to form CPT-Top I-DNA ternary complexes to stabilize the cleavable complexes and lead to apoptosis. However, they fail to enter the clinical stage due to their poor solubility in water and other biocompatible solvents as well as high toxicity. In order to improve the water-solubility and meanwhile retain the anti-tumor property of the parent compounds, many derivatives of camptothecin have been synthesized. However, only the derivatives topotecan (formula 1, 2) and irinotecan (formula 1, 3) are approved by the U.S. Food and Drug Administration to enter the clinical stage and be marketed, which are used to treat ovarian cancer, lung cancer and rectal cancer, respectively. However, topotecan and irinotecan have prominent disadvantages, including short half-life in vivo and high toxic and side effects etc. At present, there are numerous other derivatives of camptothecin in the clinical trial stage.

In addition, E lactone ring in the camptothecin molecule is an essential function moiety for the anti-cancer activity of camptothecin and derivatives thereof, and rapidly opens under a basic or physiological condition to lead to disappearance of the anti-cancer activity (formula 2). It is confirmed by several experiments that there is an equilibrium between the lactone ring structure and the open-ring structure in plasma. Moreover, a human plasma protein preferably binds to the molecule having the open-ring structure, which facilitates the equilibrium to be shifted towards the open-ring form, leads to decrease of the effective plasma concentration of this class of compounds, and thereby reduces the anti-tumor activity thereof Chemical structures of camptothecin, topotecan and irinotecan

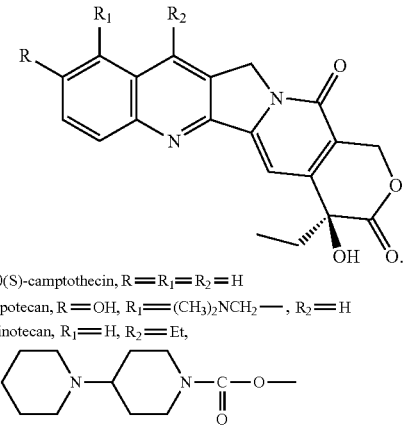

Formula 1

1. 20(S)-camptothecin, $R = R_1 = R_2 = H$
2. topotecan, $R = OH$, $R_1 = (CH_3)_2NCH_2$—, $R_2 = H$
3. irinotecan, $R_1 = H$, $R_2 = Et$, It is also confirmed by further research that the open-ring structure is the cause of adverse side effects, such as bone marrow suppression, vomiting, diarrhea, and the like.

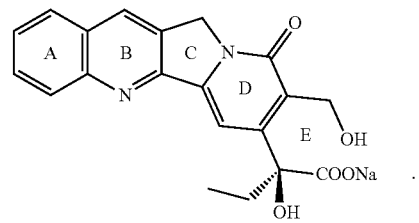

Formula 2

Equilibrium between lactone ring structure and open-ring structure of camptothecin under a basic or physiological condition In order to improve the solubility of a drug, technologies such as an emulsion technology, a micelle technology and the like are in widespread use in a formulation of a drug having poor water-solubility or water-insolubility. However, no formulation technology is applicable to camptothecin at present, because of its highly poor solubility in water and organic solvents. Therefore, there is still a need to develop new camptothecin derivatives having both higher anti-cancer activity and better solubility and stability.

The present invention provides a series of novel fat-soluble camptothecin derivatives which have better solubility in biocompatible fat-soluble solvents and can be formulated into pharmaceutical dosage forms by new formulation technologies, such as emulsions, microemulsions, micelles, liposomes, nanoparticles and the like. The novel pharmaceutical compounds of the present application are expected to improve the duration of action (half-life) and efficacy in vivo and reduce side effects thereof.

DISCLOSURE OF INVENTION

An object of the present invention is to provide novel fat-soluble anti-cancer pharmaceutical compounds. Such compounds having anti-cancer activity are soluble in biocompatible fat-soluble solvents, and are lipophilic trolox ester- or lipophilic trolox amide-modified camptothecin or camptothecin derivatives.

Another object of the present invention is to provide methods for synthesizing the fat-soluble anti-cancer pharmaceutical compounds.

Another object of the present invention is to provide preparations comprising the fat-soluble anti-cancer pharmaceutical compounds, i.e. an emulsion preparation and a micelle preparation. The emulsion preparation comprises the anti-cancer pharmaceutical compound, one or more surfactants, an oil phase (a lipophilic medium) and an aqueous phase. The micelle preparation comprises the anti-cancer pharmaceutical compound, a cosolvent, one or more surfactants and an aqueous phase.

Moreover, another object of the present invention is to provide a use of the fat-soluble anti-cancer pharmaceutical compounds in the manufacture of an anti-cancer medicament.

The fat-soluble anti-cancer pharmaceutical compounds of the present invention are the lipophilic trolox ester- or amide-modified camptothecin or camptothecin derivatives. The camptothecin or camptothecin derivatives have anti-cancer activity. The molecule of camptothecin or camptothecin derivative is covalently bonded to the molecule of the lipophilic trolox ester (or trolox amide) by a linking group (such as succinyl, glutaryl, oxydiacetyl (diglycoloyl or diglycolyl), methylene carbonyl, methylphosphono and the like) to form the fat-soluble anti-cancer pharmaceutical compound of the present invention.

The objects of the present invention are achieved by the following technical solution: trolox derivative-modified fat-soluble anti-cancer pharmaceutical compounds having a structure represented by the following formula I or II:

I

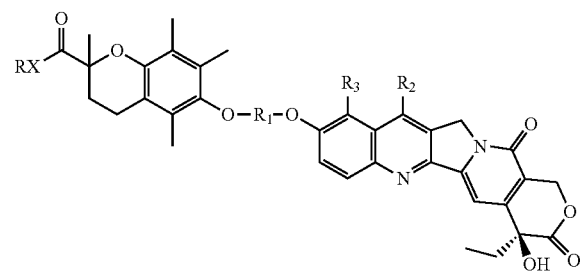

-continued

II

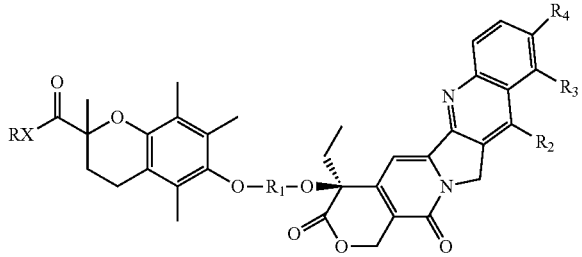

In the above structural formulae,
R is a lipophilic group selected from one of the following groups:
 a) substituted and unsubstituted linear alkyl;
 b) substituted and unsubstituted cycloalkyl;
 c) substituted and unsubstituted branched alkyl;
 d) unsaturated linear hydrocarbyl;
 e) unsaturated cyclohydrocarbyl;
 f) unsaturated branched hydrocarbyl;
 g) substituted and unsubstituted aryl; and
 h) substituted and unsubstituted aralkyl;
$R_1$ is a linking group selected from one of the following groups:
 a) —(C=O)—;
 b) —P(=O)(R')—, wherein R' is C1-C6 alkyl, C1-C6 alkoxyl or aryl;
 c) —(C=O)(CH$_2$)$_n$(C=O)—, wherein n=1-10;
 d) —(C=O)CH$_2$—O—CH$_2$(C=O)—; and
 e) —(CH$_2$)$_n$(C=O)—, wherein n=1-10;
X is —O—, —NH— or —NR'—, wherein R' is C1-C6 alkyl;
$R_2$ is H, C1-C6 alkyl or —Si(CH$_3$)$_2$tBu;
$R_3$ is H, NO$_2$, —CH$_2$N(CH$_3$)$_2$, NH$_2$ or

$R_4$ is H, C1-C6 alkyl or

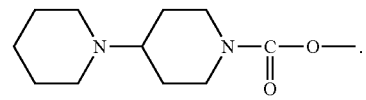

In the fat-soluble anti-cancer pharmaceutical compound of the present invention, the lipophilic moiety is trolox having the lipophilic group R, which is selected from the trolox ester or trolox amide compound.

Trolox is a water-soluble derivative of vitamin E and its chemical name is 6-hydroxy-2,5,7,8-tetramethylchroman-2-carboxylic acid, which is an antioxidant like vitamin E, and has a structure represented by formula 3. Trolox has two optically isomeric structures, R-(+)-trolox (its chemical name is R-(+)-6-hydroxy-2,5,7,8-tetramethylchroman-2-carboxylic acid) and S-(−)-trolox (its chemical name is S-(−)-6-hydroxy-2,5,7,8-tetramethylchroman-2-carboxylic acid); and its racemate is (±)-trolox (its chemical name is (±)-6-hydroxy-2,5,7,8-tetramethylchroman-2carboxylic acid).

Chemical structures of trolox,

Formula 3

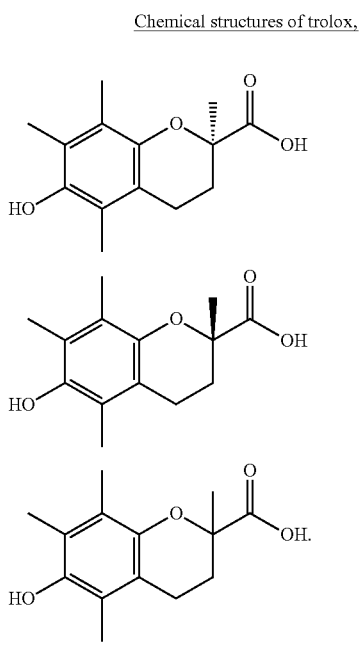

wherein A: R-(+)-trolox; B: S-(−)-trolox; C: (±)-trolox.

The trolox in the fat-soluble anti-cancer pharmaceutical compound of the present invention includes the optical isomers or racemate thereof.

Trolox ester is an ester compound obtained by reaction of the trolox with an alcoholic compound or a phenolic compound. It can be covalently bonded to the molecule of camptothecin or a camptothecin derivative having anti-cancer activity by one linking group to form the novel anti-cancer pharmaceutical compound of the present invention. The trolox ester has the chemical structure as represented by formula 4, and also has two optical isomers, i.e. R-(+)-trolox ester (its chemical name is R-(+)-6-hydroxy-2,5,7,8-tetramethylchroman-2-carboxylic acid ester) and S-(−)-trolox ester (its chemical name is S-(−)-6-hydroxy-2,5,7,8-tetramethylchroman-2-carboxylic acid ester); and a racemate thereof is (±)-trolox ester (its chemical name is (±)-6-hydroxy-2,5,7,8-tetramethylchroman-2-carboxylic acid ester). In the molecular structure, the lipophilic functional group R can be alkyl, branched alkyl or cycloalkyl, or unsaturated hydrocarbyl, unsaturated branched hydrocarbyl, unsaturated cyclohydrocarbyl, substituted and unsubstituted aryl, or substituted or unsubstituted aralkyl or the like.

Chemical structures of trolox esters,

Formula 4

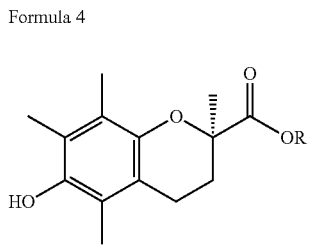

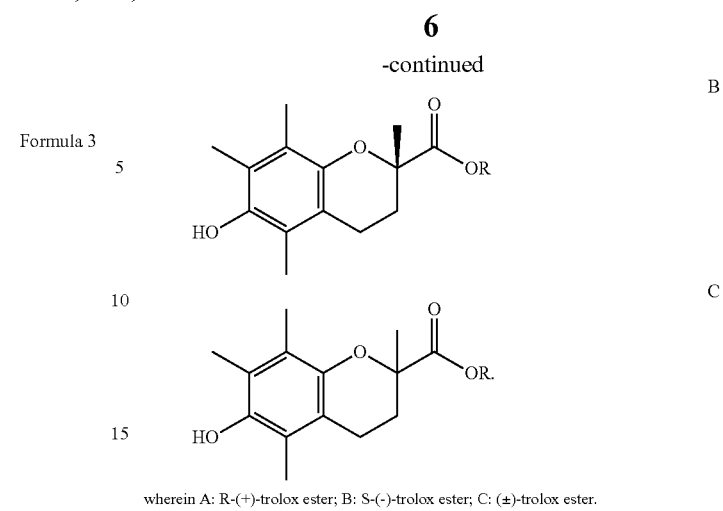

wherein A: R-(+)-trolox ester; B: S-(−)-trolox ester; C: (±)-trolox ester.

The alcohols that form trolox esters with trolox can be any aliphatic alcohols, such as saturated, unsaturated, linear, branched, cyclic aliphatic alcohols and aliphatic enols, and so on. Preferred are alcoholic compounds having a carbon atom number of ≥6, including, but not limited to, hexanol, capryl alcohol (1-octanol), 2-ethyl hexanol, pelargonic alcohol (1-nonanol), capric alcohol (1-decanol or decyl alcohol), undecyl alcohol (1-undecanol, undecanol, or hendecanol), lauryl alcohol (dodecanol or 1-dodecanol), tridecyl alcohol (1-tridecanol, tridecanol, or isotridecanol), myristyl alcohol (1-tetradecanol), pentadecyl alcohol (1-pentadecanol or pentadecanol), cetyl alcohol (1-hexadecanol), palmitoleyl alcohol (cis-9-hexadecen-1-ol), heptadecyl alcohol, stearyl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z,12Z-octadecadien-1-ol), elaidolinoleyl alcohol (9E,12E-octadecadien-1-ol), linolenyl alcohol (9Z,12Z,15Z-octadecatrien-1-ol), elaidolinolenyl alcohol (9E,12E,15E-octadecatrien-1-ol), nonadecyl alcohol (1-nonadecanol), arachidyl alcohol (1-eicosanol), eneicosyl alcohol (1-heneicosanol), behenyl alcohol (1-docosanol), erucyl alcohol (cis-13-docosen-1-ol), lignoceryl alcohol (1-tetracosanol), ceryl alcohol (1-hexacosanol), montanyl alcohol (cluytyl alcohol or 1-octacosanol), myricyl alcohol (melissyl alcohol or 1-triacontanol), geddyl alcohol (1-tetratriacontanol), and the like. The alcohols can be also other alcoholic compounds, such as benzyl alcohol, phenethyl alcohol and other aromatic alcohol compounds.

The compounds that form trolox esters with trolox also include phenolic compounds, such as phenols, alkyl phenols, alkoxy phenols, aminophenols, halophenols, multi-substituted phenols, or 1-naphthol, 2-naphthol, alkyl naphthols, alkoxy naphthols, halonaphthols, multi-substituted naphthols, and the like.

Trolox amide is an amide compound obtained by reaction of trolox with an amine compound (a primary or secondary amine). It can be covalently bonded to the molecule of camptothecin or a camptothecin derivative having anti-cancer activity by one linking group to form the novel anti-cancer pharmaceutical compound of the present invention. The trolox amide has the chemical structure as represented by formula 5, and also has two optical isomers, i.e. R-(+)-trolox amide (its chemical name is R-(+)-6-hydroxy-2,5,7,8-tetramethylchroman-2-carboxamide) and S-(−)-trolox amide (its chemical name is S-(−)-6-hydroxy-2,5,7,8-tetramethylchroman-2-carboxamide); and a racemate thereof is (±)-trolox amide (its chemical name is (±)-6-hydroxy-2,5,7,8-tetramethylchroman-2-carboxamide). In the molecular structure, the functional group R can be alkyl, branched alkyl or cycloalkyl, or unsaturated hydrocarbyl, unsaturated branched hydrocarbyl, unsaturated cyclohydrocarbyl, substituted and unsubstituted aryl, or substituted or unsubstituted aralkyl or the like. The substituent R preferably has a carbon atom number of ≥6. In the molecular structure, the substituent $R_1$ is preferably H, —$CH_3$, —$CH_2CH_3$, —$CH_2CH_2CH_3$, —$CH_2CH_2CH_2CH_3$, —$CH_2CH_2CH_2CH_2CH_3$ or —$CH_2CH_2CH_2CH_2CH_2CH_3$.

Amine compounds that form trolox amides with trolox can be any primary or secondary amines, including aliphatic amines or aromatic amines, such as saturated, unsaturated, linear, branched, cyclic aliphatic amines, aromatic amines, aralkyl amines, and the like.

Chemical structures of trolox amides,

Formula 5

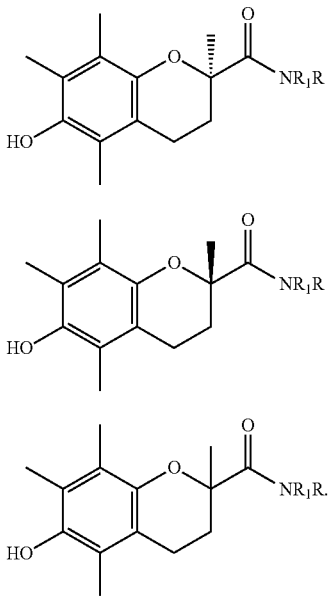

wherein A: R-(+)-trolox amide; B: S-(-)-trolox amide; C: (±)-trolox amide.

In the molecule of the fat-soluble anti-cancer pharmaceutical compound of the present invention, the anti-cancer pharmaceutically active moiety is the camptothecin or camptothecin derivative having anti-cancer activity, and the structural formula thereof is represented by formula 6, wherein $R_2$ is H, C1-C6 alkyl or —$Si(CH_3)_2tBu$; $R_3$ is H, $NO_2$, —$CH_2N(CH_3)_2$, $NH_2$ or

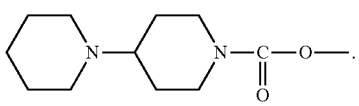 [SMILES: COC(=O)N1CCC(N2CCCCC2)CC1]

$R_4$ is H, OH, C1-C6 alkyl or

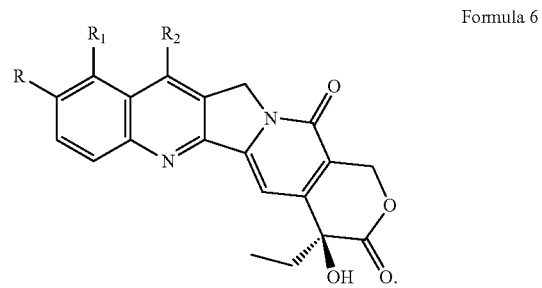

Chemical structure of the molecule of camptotecin or camptothecin derivative.

Formula 6

In the molecule of the fat-soluble anti-cancer pharmaceutical compound of the present invention, the anti-cancer active moiety is preferably camptothecin (1), 10-hydroxycamptothecin (2) or 7-ethyl-10-hydroxycamptothecin (3), and the molecular structure thereof is represented by formula 7. They can be covalently boned to trolox esters (or trolox amides) by the linking group to form the fat-soluble anti-cancer pharmaceutical compounds of the present invention, respectively.

Preferred chemical structure of camptothecin or camptothecin derivative.

Formula 7

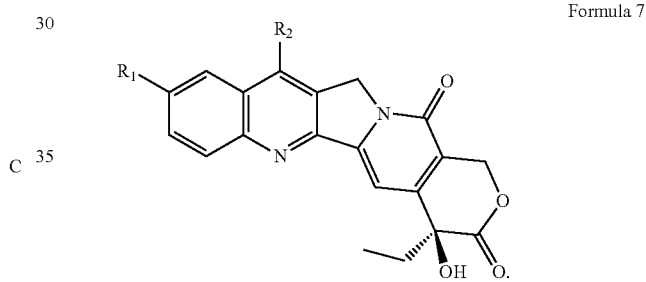

1. 20(S)-camptothecin: $R_1$=$R_2$=H
2. 10-hydroxycamptothecin: $R_1$=OH, $R_2$=H
3. 7-ethyl-10-hydroxycamptothecin: $R_1$=OH, $R_2$=Et The molecule of the fat-soluble anti-cancer pharmaceutical compound of the present invention comprises the anti-cancer pharmaceutically active moiety and the lipophilic moiety. The two moieties are covalently bonded together by the linking group to form the novel fat-soluble anti-cancer pharmaceutical compound. The anti-cancer pharmaceutically active moiety is the camptothecin or camptothecin derivative, wherein the camptothecin or camptothecin derivative comprises a phenolic hydroxy or a hydroxy on a lactone ring, and the hydroxy can form an ester bond with carboxy, chloroacyl or phosphono (phosphoryl) group. The lipophilic moiety is the trolox ester (or trolox amide) which is a fat-soluble compound and has one phenolic hydroxy that can form an ester bond with carboxy or phosphono (phosphoryl) group or form an ether bond by reacting with a halide. Therefore, the camptothecin or camptothecin derivative can be covalently bonded to the lipophilic trolox ester (or trolox amide) by a bifunctional linking group to form the molecule of a novel anti-cancer pharmaceutical compound of the present invention. For example, the trolox ester (or trolox amide) is covalently bonded to the anti-cancer pharmaceutical compound camptothecin, 10-hydroxycamptothecin or 7-ethyl-10-hydroxycamptothecin (SN-38) by one linking group (such as succinyl, glutaryl, diglycolyl, methylene carbonyl) to form the novel fat-soluble anti-cancer pharmaceutical compound.

The linking group is provided by a linking molecule comprising two or more active groups, such as carbonyl —(C=O)— that is provided by oxalyl chloride (O=CCl$_2$), —P(=O)(OR')— group that is provided by phosphoryl dichloride (O=POR'Cl$_2$), alkylenecarbonyl (—(CH$_2$)$_n$CO—) that is provided by halocarboxylic acid or halocarboxylate, succinyl, glutaryl, oxydiacetyl (diglycoloyl or diglycolyl) and the like that are provided by a different binary carboxylic acid (CH$_2$)$_n$(COOH)$_2$ or a cyclic anhydride

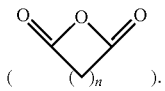

Comparing with the parent compounds having anti-cancer activity (camptothecin Or camptothecin derivatives, such as 10-hydroxycamptothecin and 7-ethyl-10-hydroxycamptothecin), the novel anti-cancer pharmaceutical compounds of the present invention have better lipophilicity (oleophilicity). The novel compounds of the present invention comprise anti-cancer pharmaceutical parent compound moieties and lipophilic group moieties. The anti-cancer pharmaceutical parent compound molecules are covalently bonded to oleophilic molecules by linking groups to form the novel anti-cancer pharmaceutical compounds of the present invention.

The present invention also relates to a method for preparing a trolox derivative-modified fat-soluble anti-cancer pharmaceutical compound, comprising the following steps:

1) esterifying/amidating a trolox with an alcohol or a phenol/amine to produce a trolox ester/trolox amide;

2) esterifying/etherifying a phenolic hydroxy of the trolox ester or the trolox amide with a linking molecule to produce a derivative of the trolox ester or a derivative of the trolox amide;

3) esterifying the derivative of the trolox ester or the derivative of the trolox amide obtained in step 2) or an acyl chloride thereof with camptothecin or its derivative to produce the trolox derivative-modified fat-soluble anti-cancer pharmaceutical compound;

The linking molecule is one of the following molecules comprising two or more active groups:

(1) oxalyl chloride O=CCl$_2$;

(2) an alkyl, alkoxy or aryl phosphoryl dichloride O=POR'Cl$_2$, wherein R' is C1-C6 alkyl, C1-C6 alkoxy or aryl;

(3) a binary carboxylic acid (CH$_2$)$_n$(COOH)$_2$ or a cyclic anhydride

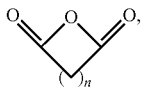

wherein n=1-10;

(4) diglycolic acid or diglycolic anhydride;

(5) a halocarboxylic acid or a halocarboxylate Z—(CH$_2$)$_n$COOR', wherein n=1-10, Z is Cl, Br or I, and R' is alkyl.

More specifically and preferably, the method comprises the following steps:

1) reacting trolox (1) with an alcohol or a phenol (2) in the presence of 4-dimethylaminopyridine (DMAP) and 2-chloro-1-methylpyridinium iodide (CMPI) as catalysts or N,N'-dicyclohexylcarbodiimide (DCC) and 4-dimethylaminopyridine (DMAP) as catalysts, to produce a trolox ester (3); or reacting trolox (1) with an amine (8) in the presence of N,N'-dicyclohexylcarbodiimide (DCC) as a catalyst to produce a trolox amide (9).

2) esterifying or etherifying the trolox ester (3) or trolox amide (9) with a linking molecule according to one of the following processes to produce a derivative of the trolox ester or a derivative of the trolox amide:

a) reacting the trolox ester (3) or trolox amide (9) with a cyclic anhydride

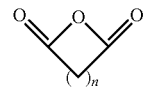

or diglycolic anhydride in the presence of tin (II) 2-ethylhexanoate or cesium carbonate as a catalyst; or reacting the trolox ester (3) or trolox amide (9) with an excessive amount of a binary carboxylic acid (CH$_2$)$_n$(COOH)$_2$ or diglycolic acid in the presence of 4-dimethylaminopyridine (DMAP) and 2-chloro-1-methylpyridinium iodide (CMPI) as catalysts or N,N'-dicyclohexylcarbodiimide (DCC) and 4-dimethylaminopyridine (DMAP) as catalysts, to produce the derivative of the trolox ester (4) or the derivative of the trolox amide (10), respectively;

b) in the presence of a base (such as triethylamine, pyridine, sodium carbonate, potassium carbonate, cesium carbonate) as a catalyst, reacting the trolox ester (3) or trolox amide (9) with a halocarboxylic acid to produce the derivative of the trolox ester (15a, R'=H) or the derivative of the trolox amide (15a), or reacting the trolox ester (3) or trolox amide (9) with a halocarboxylate, and then dealkylating the resulting product (15b, R'=alkyl) to produce the derivative of the trolox ester (15a) or the derivative of the trolox amide (15a);

c) reacting the trolox ester (3) or trolox amide (9) with an alkyl phosphonyl (phosphoryl) dichloride, an alkoxy phosphonyl (phosphoryl) dichloride or an aryl phosphonyl (phosphoryl) dichloride in the presence of a base (such as triethylamine, pyridine, sodium carbonate, potassium carbonate, cesium carbonate) as a catalyst, to produce the derivative of the trolox ester (19) or the derivative of the trolox amide (19);

d) reacting the trolox ester (3) or trolox amide (9) with oxalyl chloride in the presence of a base (such as triethylamine or pyridine) as a catalyst, to produce the derivative of the trolox ester or the derivative of the trolox amide;

3) reacting the derivative of the trolox ester (4, 15a) or the derivative of the trolox amide (10, 15a) obtained in a) or b) of step 2) with thionyl (di)chloride to produce an acyl chloride product (5, 11 or 16), respectively;

4) reacting the derivative of the trolox ester (4, 15a) or the derivative of the trolox amide (10, 15a) directly with camptothecin or its derivative in the presence of 4-dimethylaminopyridine (DMAP) and 2-chloro-1-methylpyridinium iodide (CMPI) as catalysts or N,N'-dicyclohexylcarbodiimide (DCC) and 4-dimethylaminopyridine (DMAP) as catalysts, to produce a trolox derivative-modified fat-soluble anti-cancer pharmaceutical compound (6, 12, 13, 14, 17 or 18); or 5) reacting the acyl chloride product (5, 11 or 16) obtained in step 3) or the derivative of the trolox ester (19) or the derivative of the trolox amide (19) obtained in c) or d) of step 2) directly with camptothecin or its derivative in the presence of a base (such as triethylamine, pyridine, sodium carbonate, potassium carbonate, cesium carbonate) as a catalyst, to produce a trolox derivative-modified fat-soluble anti-cancer pharmaceutical compound (6, 12, 13, 14, 17, 18, 20 or 21).

Scheme 8 illustrates a synthetic route, in which trolox (1) is reacted with an alcohol or a phenol (2) in the presence of 4-dimethylaminopyridine (DMAP) and 2-chloro-1-methylpyridinium iodide (CMPI) as catalysts or N,N'-dicyclohexylcarbodiimide (DCC) and 4-dimethylaminopyridine (DMAP) as catalysts to produce a trolox ester (3), which is then reacted with a cyclic anhydride (such as succinic anhydride, glutaric anhydride, diglycolic anhydride and the like) in the presence of tin (II) 2-ethylhexanoate (or cesium carbonate) as a catalyst to produce a derivative of the trolox ester (4). The trolox ester (3) can be also reacted with an excessive amount of a binary carboxylic acid having a bifunctional group (such as succinic acid, glutaric acid, diglycolic acid and other binary carboxylic acids) in the presence of 4-dimethylaminopyridine (DMAP) and 2-chloro-1-methylpyridinium iodide (CMPI) as catalysts or N,N'-dicyclohexylcarbodiimide (DCC) and 4-dimethylaminopyridine (DMAP) as catalysts, to produce a derivative of the trolox ester (4). The compound (4) is further reacted with thionyl (di)chloride to produce an acyl chloride derivative (5) of the trolox ester. The acyl chloride functional group of the compound (5) is then selectively reacted with a phenolic hydroxy of 10-hydroxy-substituted camptothecin, such as 10-hydroxycamptothecin or 7-ethyl-10-hydroxycamptothecin, in the presence of a base (such as triethylamine) as a catalyst, to produce a fat-soluble anti-cancer pharmaceutical compound (6) of the present invention. The derivative of the trolox ester (4) can be also reacted directly with 10-hydroxy-substituted camptothecin, such as 10-hydroxycamptothecin or 7-ethyl-10-hydroxycamptothecin, in the presence of 4-dimethylaminopyridine (DMAP) and 2-chloro-1-methylpyridinium iodide (CMPI) as catalysts or N,N'-dicyclohexylcarbodiimide (DCC) and 4-dimethylaminopyridine (DMAP) as catalysts, to produce the fat-soluble anti-cancer pharmaceutical compound (6) of the present invention.

Scheme 8. Synthetic route 1 of the novel anti-cancer pharmaceutical compound

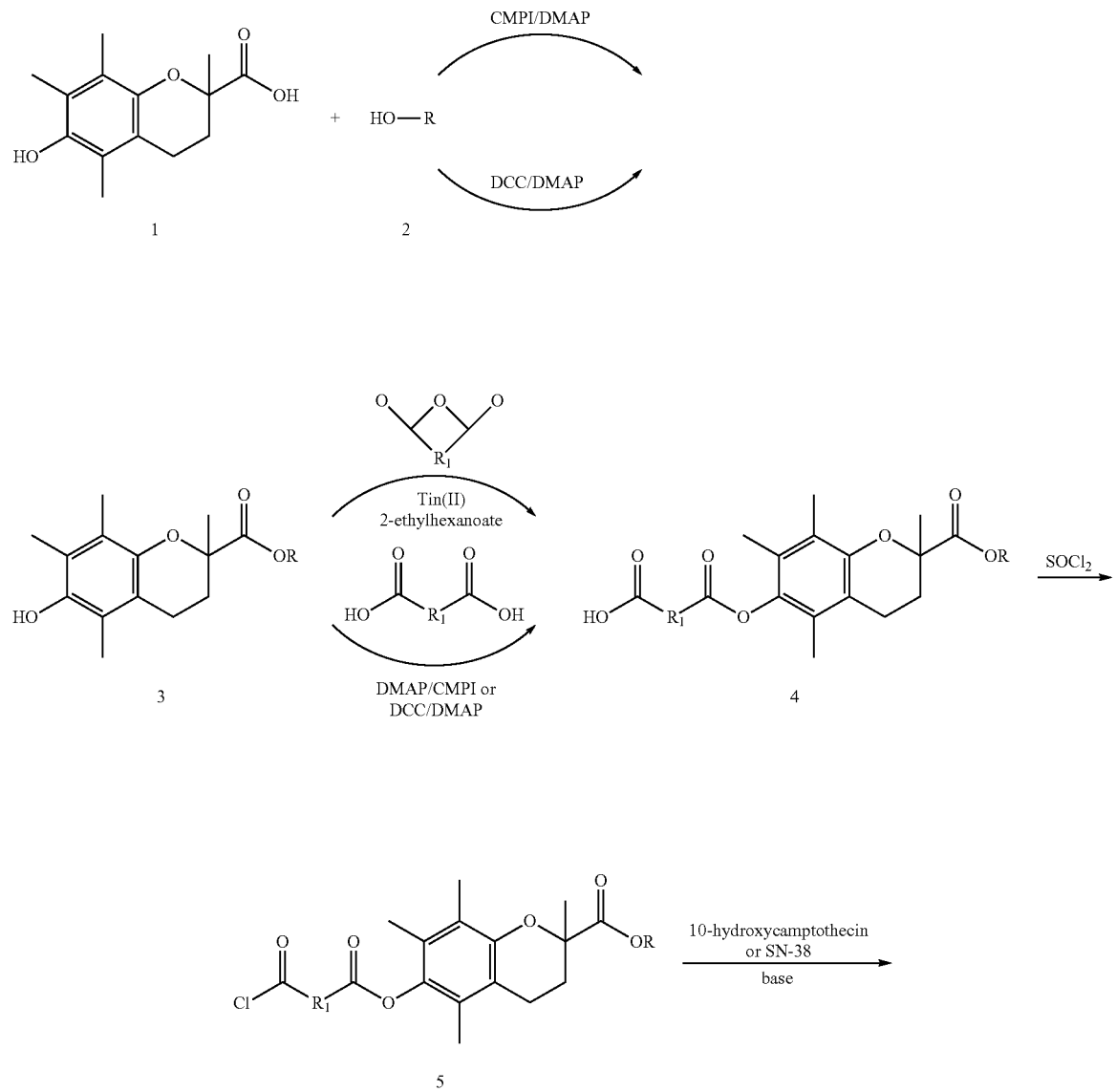

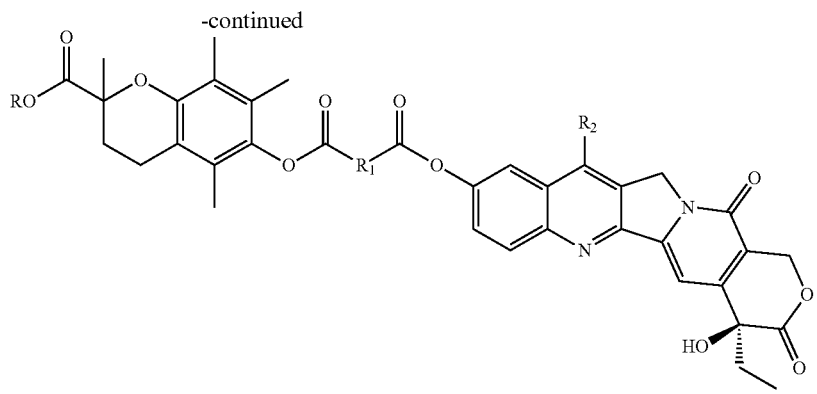

6

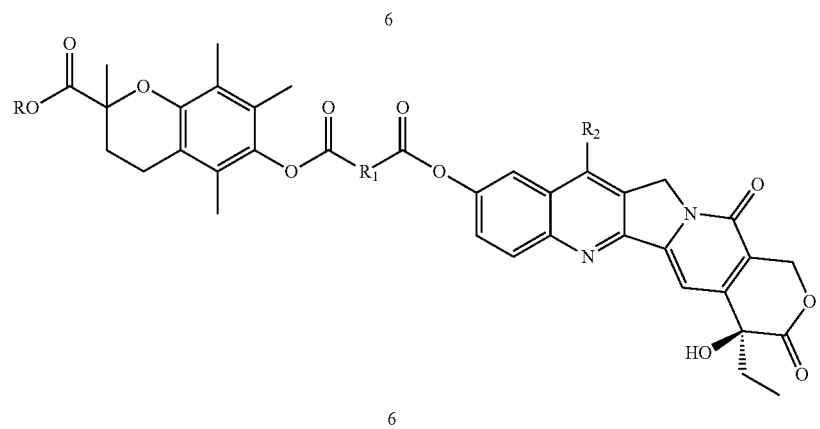

6

R: alkyl, branched alkyl or cycloalkyl, or unsaturated hydrocarbyl, unsaturated branched hydrocarbyl, unsaturated cyclohydrocarbyl, aryl or aralkyl or the like; $R_1$: —$CH_2CH_2$—, —$CH_2CH_2CH_2$—, —$CH_2OCH_2$— or the like; $R_2$: H, —$CH_2CH_3$ or the like.

Scheme 9 illustrates another synthetic route of the fat-soluble anti-cancer pharmaceutical compounds of the present invention, in which the acyl chloride derivative (5) of the trolox ester is reacted with the hydroxy on the lactone ring of camptothecin (or its derivative) under the action of a base (such as triethylamine) to produce the novel anti-cancer pharmaceutical compound (7) of the present invention. The derivative of the trolox ester (4) can be also reacted directly with camptothecin (or its derivative) in the presence of 4-dimethylaminopyridine (DMAP) and 2-chloro-1-methylpyridinium iodide (CMPI) as catalysts or N,N'-dicyclohexylcarbodiimide (DCC) and 4-dimethylaminopyridine (DMAP) as catalysts, to produce the novel anti-cancer pharmaceutical compound (7) of the present invention.

Scheme 9.
Synthetic route 2 of the novel anti-cancer pharmaceutical compound

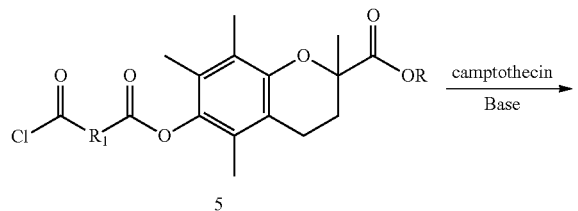

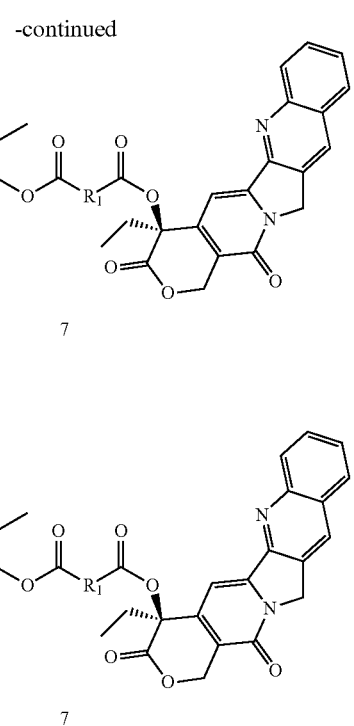

R: alkyl, branched alkyl or cycloalkyl, or unsaturated hydrocarbyl, unsaturated branched hydrocarbyl, unsaturated cyclohydrocarbyl, aryl or aralkyl or the like; $R_1$: —$CH_2CH_2$—, —$CH_2CH_2CH_2$—, —$CH_2OCH_2$— or the like;

Scheme 10 illustrates another synthetic route of the fat-soluble anti-cancer pharmaceutical compounds of the present invention, in which the trolox (1) is reacted with an amine (8) in the presence of N,N'-dicyclohexylcarbodiimide (DCC) as a coupling agent to produce a trolox amide (9), which is then reacted with a cyclic anhydride (such as succinic anhydride, glutaric anhydride, diglycolic anhydride and the like) in the presence of tin (II) 2-ethylhexanoate or cesium carbonate as a catalyst to produce a derivative of the trolox amide (10). The compound (10) is further reacted with camptothecin, 10-hydroxycamptothecin or 7-ethyl-10-hydroxycamptothecin or the like in the presence of 4-dimethylaminopyridine (DMAP) and 2-chloro-1-methylpyridinium iodide (CMPI) as catalysts or N,N'-dicyclohexylcarbodiimide (DCC) and 4-dimethylaminopyridine (DMAP) as catalysts, to produce novel anti-cancer pharmaceutical compounds (12), (13) and (14) of the present invention, respectively. The compound (10) can be also reacted with a thionyl (di)chloride to produce an acyl chloride derivative of the trolox ester (11). The acyl chloride functional group of the compound (II) is then selectively reacted with the phenolic hydroxy of 10-hydroxy-substituted camptothecin, such as 10-hydroxycamptothecin or 7-ethyl-10-hydroxycamptothecin, or reacted with the hydroxy on the lactone ring of camptothecin (or its derivative), in the presence of a base (such as triethylamine) as a catalyst, to produce the fat-soluble anti-cancer pharmaceutical compounds (12), (13) and (14) of the present invention.

Scheme 10. Synthetic route 3 of novel anti-cancer pharmaceutical compounds

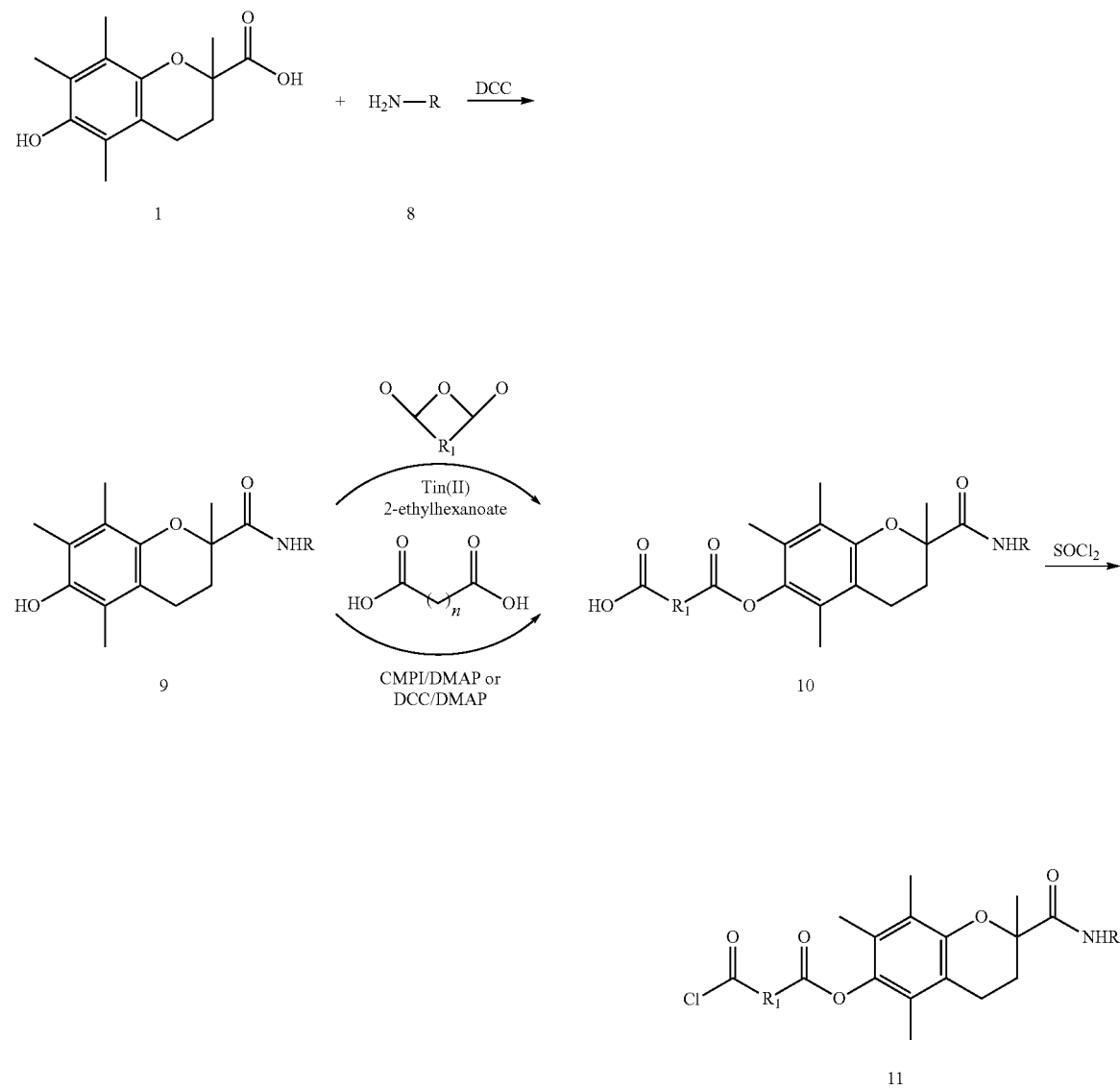

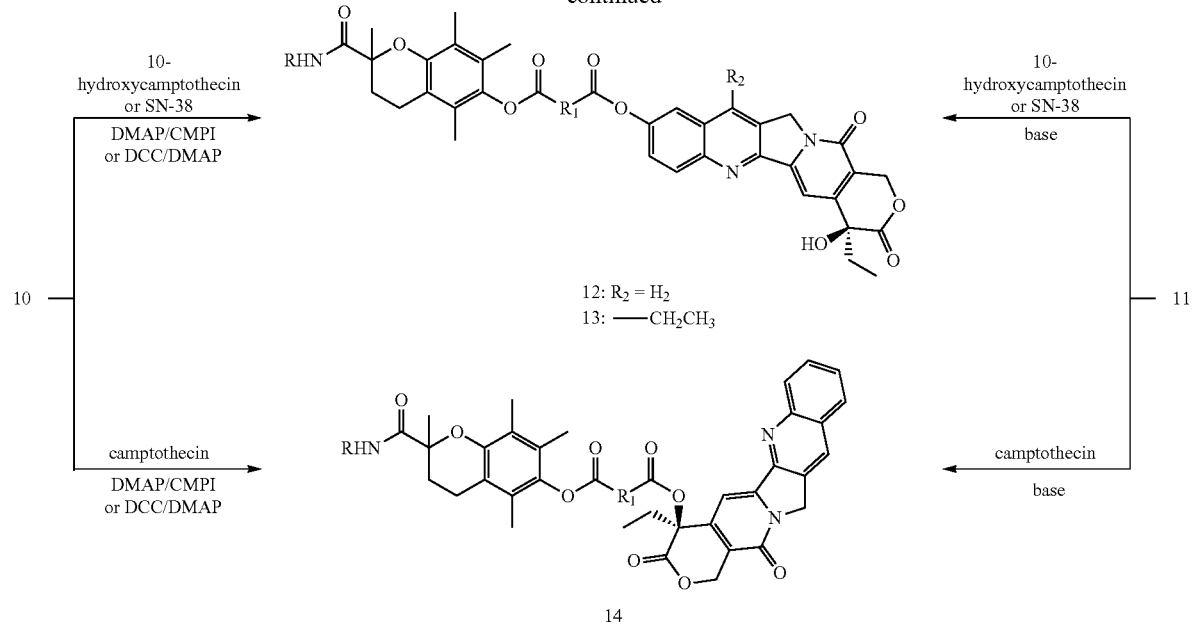

R: alkyl, branched alkyl or cycloalkyl, or unsaturated alkenyl, unsaturated branched alkenyl, unsaturated cycloalkenyl, aryl or aralkyl or the like; $R_1$: —$CH_2CH_2$—, —$CH_2CH_2CH_2$—, —$CH_2OCH_2$— or the like; $R_2$: H, —$CH_2CH_3$ or the like.

Schemes 11 and 12 illustrate other synthetic routes of the fat-soluble anti-cancer pharmaceutical compounds of the present invention, in which in the presence of a base (such as triethylamine, pyridine, sodium carbonate, potassium carbonate, and cesium carbonate) as a catalyst, a trolox ester (3) or a trolox amide (9) is reacted with a halo-(iodo-, bromo-, chloro-)carboxylic acid (such as bromoacetic acid) to produce a derivative of the trolox ester (15a), or reacted with a halocarboxylate (such as ethyl bromoacetate) to produce (15b) which is then reacted with lithium hydroxide and subsequently treated with an acid to produce (15a). The compound (15a) is reacted with thionyl (di)chloride to produce an acyl chloride derivative (16). Then the acyl chloride functional group of the compound (16) is selectively reacted with the phenolic hydroxyl of 10-hydroxyl-substituted camptothecin, such as 10-hydroxycamptothecin or 7-ethyl-10-hydroxycamptothecin, or reacted with the hydroxyl on the lactone ring of camptothecin (or its derivative), in the presence of a base (such as triethylamine) as a catalyst, to produce fat-soluble anti-cancer pharmaceutical compounds (17) and (18) of the present invention. The derivative of the trolox ester (15a) can be also reacted directly with 10-hydroxy-substituted camptothecin (such as 10-hydroxycamptothecin or 7-ethyl-10-hydroxycamptothecin) or camptothecin in the presence of 4-dimethylaminopyridine (DMAP) and 2-chloro-1-methylpyridinium iodide (CMPI) as catalysts or N,N'-dicyclohexylcarbodiimide (DCC) and 4-dimethylaminopyridine (DMAP) as catalysts, to produce the fat-soluble anti-cancer pharmaceutical compounds (17) and (18) of the present invention, respectively.

Scheme 13 describes another synthetic route of the fat-soluble anti-cancer pharmaceutical compounds of the present invention, in which in the presence of a base (such as triethylamine, pyridine, sodium carbonate, potassium carbonate, cesium carbonate) as a catalyst, the trolox ester (3) or the trolox amide (9) is reacted with an alkyl(alkoxy) phosphonyl (phosphoryl) dichloride (such as methyl(methoxy) phosphonyl (phosphoryl) dichloride) or an aryl(aryloxy) phosphonyl (phosphoryl) dichloride (such as phenyl(phenoxy) phosphonyl (phosphoryl) dichloride) to produce a derivative of the trolox ester (19). The compound (19) is reacted directly with camptothecin or its derivative to produce trolox derivative-modified fat-soluble anti-cancer pharmaceutical compounds (20) and (21).

Scheme 11. Synthetic route 4 of the novel anti-cancer pharmaceutical compound

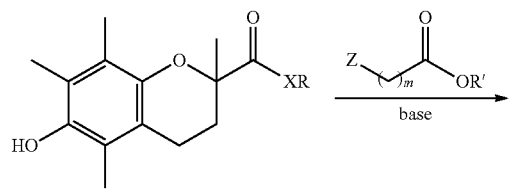

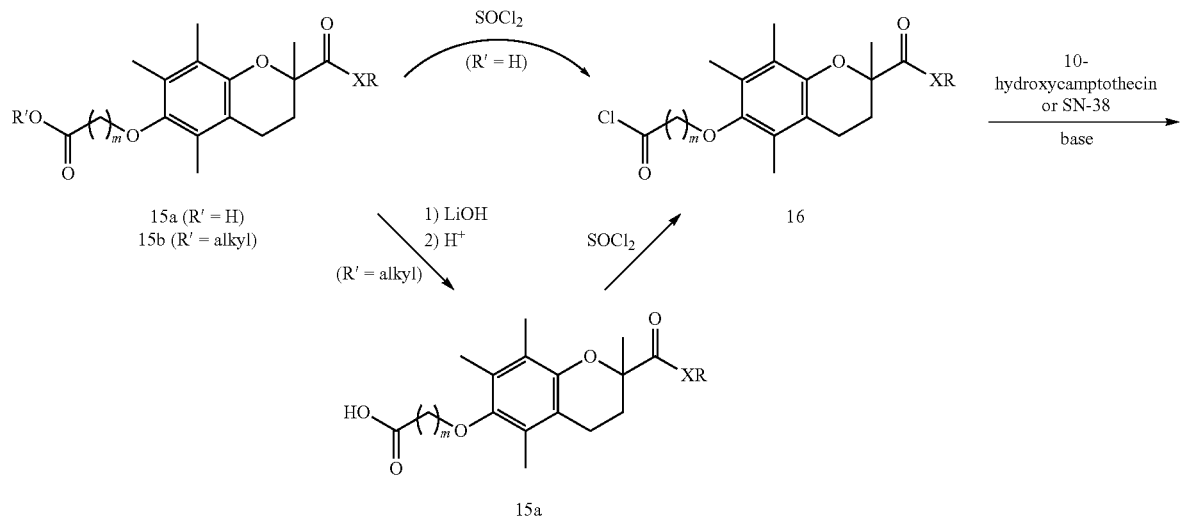
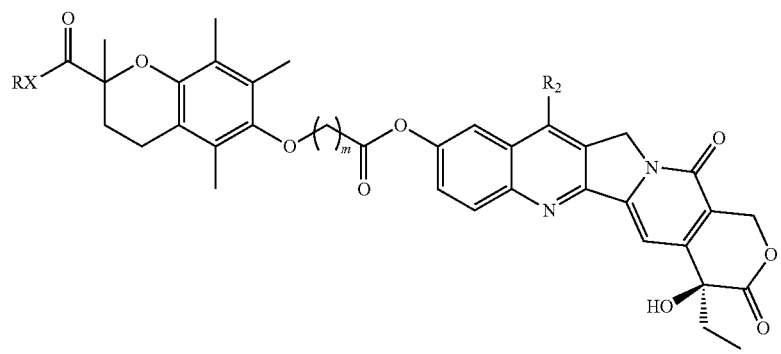
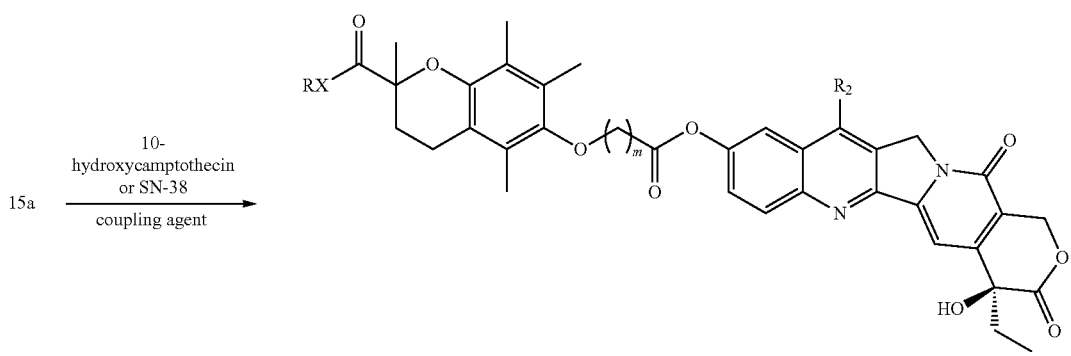

R: alkyl, branched alkyl or cycloalkyl, or unsaturated linear hydrocarbyl, unsaturated branched hydrocarbyl, unsaturated cyclohydrocarbyl, aryl or aralkyl or the like; X is —O—, —NH— or —NR'—, wherein R' is C1-C6 alkyl; m=1-10; $R_2$: H, —$CH_2CH_3$ or the like.

Scheme 12. Synthetic route 5 of the novel anti-cancer pharmaceutical compound

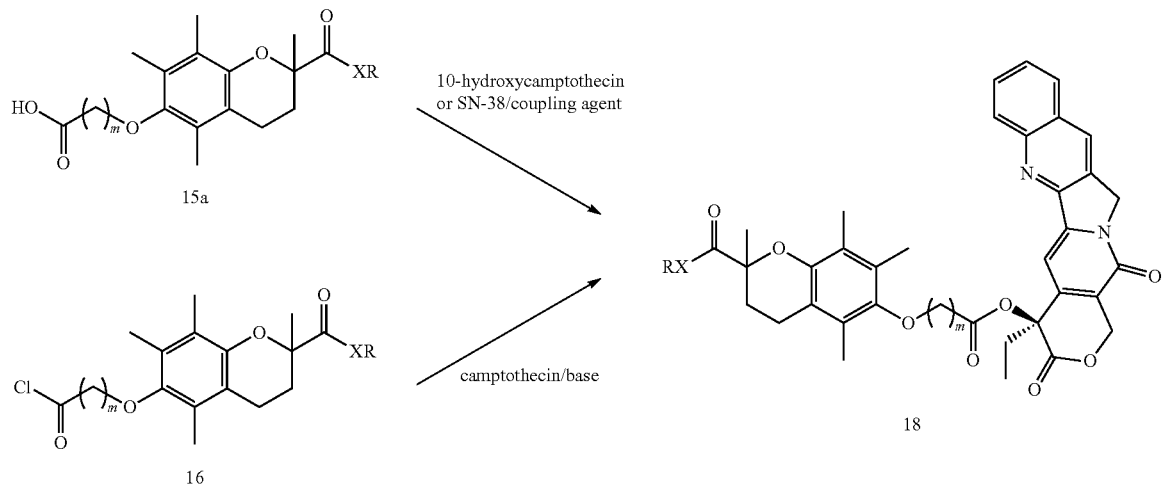

R: alkyl, branched alkyl or cycloalkyl, or unsaturated linear hydrocarbyl, unsaturated branched hydrocarbyl, unsaturated cyclohydrocarbyl, aryl or aralkyl or the like; X is —O—, —NH— or —NR'—, wherein R' is C1-C6 alkyl; m=1-10.

Scheme 13. Synthetic route 6 of the novel anti-cancer pharmaceutical compounds

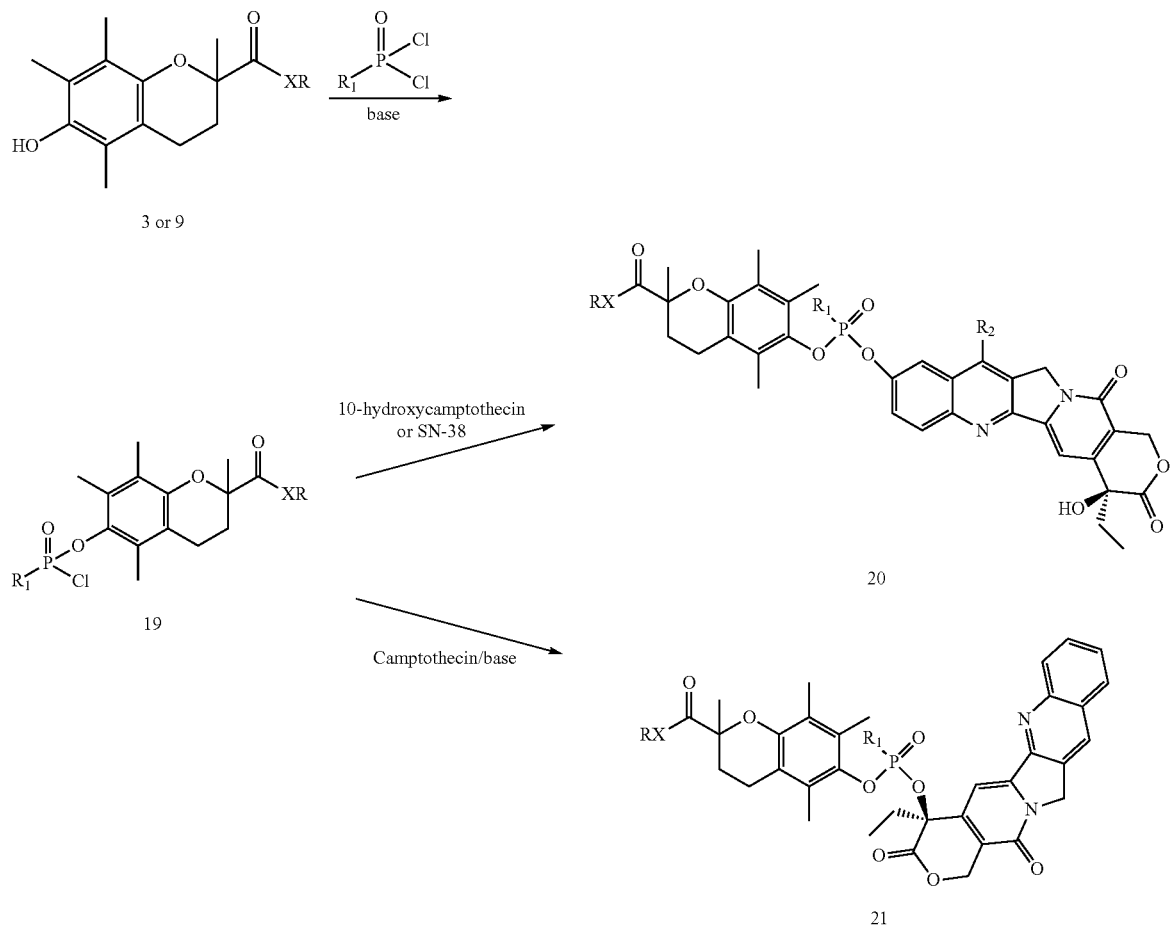

R: alkyl, branched alkyl or cycloalkyl, or unsaturated linear hydrocarbyl, unsaturated branched hydrocarbyl, unsaturated cyclohydrocarbyl, aryl or aralkyl or the like; X is —O—, —NH— or —NR'—, wherein R' is C1-C6 alkyl; $R_1$: C1-C6 alkyl, phenyl or substituted phenyl, or R'O—, R': C1-C6 alkyl, phenyl or substituted phenyl; $R_2$: H, —CH$_2$CH$_3$.

The present invention also relates to preparations of the novel fat-soluble anti-cancer pharmaceutical compound, including an emulsion preparation and a micelle preparation. The emulsion preparation comprises the novel anti-cancer pharmaceutical compound of the present invention, one or more surfactants, an oil phase (a lipophilic medium) and an aqueous phase. The emulsion can be oil-in-water or water-in-oil. The micelle preparation comprises the novel anti-cancer pharmaceutical compound of the present invention, a cosolvent and one or more surfactants and an aqueous phase.

One embodiment is an emulsion preparation or a microemulsion preparation of the fat-soluble anti-cancer pharmaceutical compound, which comprises:

1) an oil phase including
 a) the trolox derivative-modified fat-soluble anti-cancer pharmaceutical compound having a structure as represented by formula I or II;
 b) a biocompatible lipophilic medium;
2) a surfactant and a cosolvent; and
3) an aqueous phase.

Alternatively, a micelle preparation of the fat-soluble anti-cancer pharmaceutical compound comprises:

1) the trolox derivative-modified fat-soluble anti-cancer pharmaceutical compound having a structure as represented by formula I or II;
2) a surfactant;
3) a cosolvent; and
4) an aqueous phase.

The anti-cancer pharmaceutical compounds of the present invention are soluble in a lipophilic medium. The lipophilic medium (or carrier) can be any biocompatible lipophilic medium. The representative biocompatible lipophilic medium includes:

a) fat-soluble vitamin E and derivatives thereof: Vitamin E refers to natural or synthetic vitamin E series, which are usually called as tocopherols and tocotrienols; the tocopherols include α-tocopherols (D-, DL-, and L-types), β-tocopherols (D-, DL-, and L-types), γ-tocopherols (D-, DL-, and L-types), and δ-tocopherols (D-, DL-, and L-type); the tocotrienols have chemical structures similar to those of tocopherols, but the tocotrienols have three double-bonds on phytyl side chain at carbon-2; the tocotrienols include α-tocotrienols (D-, DL-, and L-types), β-tocotrienols (D-, DL-, and L-types), γ-tocotrienols (D-, DL-, and L-types), and δ-tocotrienols (D-, DL-, and L-types). The vitamin E derivatives include all derivatives of tocopherols and tocotrienols, such as vitamin E succinate, vitamin E acetate and the like;

b) greases that can be used as the lipophilic media, including fatty acids with different chain lengths and esters thereof, most of which are linear, but can be also branched, such as capric acid, caprylic acid, hexanoic acid, lauric acid, myristic acid, stearic acid, oleic acid, linoleic acid, and other saturated or unsaturated fatty acids and esters thereof;

c) monoglycerides, diglycerides or triglycerides that are formed by esterification reaction of fatty acids with glycerol, all of which can be used as the lipophilic media no matter they are synthetic or natural, for example, glycerides, such as soybean oil, cottonseed oil, rapeseed oil, fish oil, acetylated monoglycerides, glyceryl monooleate, glyceryl triacetate and diacetyl tartrate, monoglycerides, castor oil and the like; and d) fatty alcohols, such as benzyl alcohol, stearyl alcohol, lauryl alcohol, and the like, or their esters or ethers, such as benzyl benzoate.

Representative surfactants include:

a) polyethylene glycol surfactants, such as Cremophor™ EL, Tween™ series surfactants.

b) phospholipid surfactants, such as lecithin, pegylated phospholipids.

c) polyethylene glycol vitamin E derivatives, such as vitamin E polyethylene glycol succinates (such as d-α-tocopherol polyethylene glycol 1000 succinate, TPGS).

d) polyoxyethylene-polyoxypropylene block copolymers: Poloxamers or Pluronics™ block copolymers (H(OCH$_2$CH$_2$)$_a$(OCH$_2$CH$_2$CH$_2$)$_b$(OCH$_2$CH$_2$)$_a$OH).

Representative organic cosolvents include: ethanol, polyethylene glycol, propylene glycol, glycerol, N-methylpyrrolidone and the like. Polyethylene glycol (PEG) is hydrophilic, and its repeating unit has a chemical structure as represented by —CH$_2$CH$_2$O—. Polyethylene glycol (PEG) has a general formula of H—(CH$_2$CH$_2$)$_n$—OH and a molecular weight usually ranging from 200 to 10,000, e.g. polyethylene glycol 200, PEG-300, polyethylene glycol 400, and the like.

All the emulsion, microemulsion and micelle preparations according to the present invention comprise the fat-soluble anti-cancer pharmaceutical compounds of the present invention.

The "emulsion", as used herein, refers to a heterogeneous liquid dispersion system formed by dispersing one liquid phase in the form of droplets in another liquid phase under the action of a surfactant, such as droplets formed from oil and water, and its diameter is generally 0.1 to 3.0 microns.

The emulsion may form a stable microemulsion. The term "microemulsion" refers to a thermodynamically stable, isotropic, transparent or translucent dispersion system formed from two immiscible liquids. For example, a microemulsion dispersion system formed from oil and water is stabilized by an interfacial membrane formed from surfactant molecules. The microemulsion has an average droplet diameter of less than 200 nm, usually from 10 nm to 50 nm.

The emulsion or microemulsion comprises an oil phase and an aqueous phase. The emulsion or microemulsion can be oil-in-water or water-in-oil.

In the absence of water, a homogeneous transparent solution formed by mixing an oil phase, a non-ionic surfactant, a co-emulsifier and the pharmaceutical compound is called as a self-emulsifying drug delivery system (SEDDS), which is self-emulsified to form an emulsion having a particle size of 100 nm to 500 nm, and can be used to improve the solubility and oral absorbability of a lipophilic drug.

The anti-cancer pharmaceutical compound of the present invention is comprised in the emulsion or microemulsion preparation in an amount in the range of 0.005 wt % to 5.0 wt %, preferably 0.01 wt % to 2.5 wt %, more preferably 0.1 wt % to 1.5 wt %.

The lipophilic medium is comprised in the emulsion or microemulsion preparation in an amount in the range of 2 wt % to 20 wt %, preferably 4 wt % to 12 wt %, more preferably 6 wt to 10 wt %.

In one embodiment of the emulsion or microemulsion, the lipophilic medium comprises soybean oil, and the aqueous medium is water. In another embodiment of the emulsion and microemulsion, the lipophilic medium comprises an oil-soluble vitamin E. In another embodiment of the emulsion or microemulsion, the lipophilic medium comprises a derivative of an oil-soluble vitamin E.

In addition to the anti-cancer pharmaceutical compound of the present invention, the emulsion or microemulsion preparation can further comprises other ingredients conventionally used in pharmaceutical emulsion and microemulsion preparations. These ingredients include surfactants and cosolvents. Representative surfactants include nonionic surfactants, such as Cremophor EL, Tween 80, polyethylene glycol vitamin E derivative surfactants and other surfactant polymers.

Suitable polyethylene glycol vitamin E derivative surfactants include vitamin E polyethylene glycol succinate derivatives (such as vitamin E polyethylene glycol succinate). In the molecules of vitamin E derivatives, polyethylene glycol is linked with the hydroxyl of vitamin E via succinic acid. The polyethylene glycol in these polyethylene glycol derivatives of vitamin E can have various molecular weights (such as 200, 3000, 400, 6000, 1,000 etc). Herein, "vitamin E polyethylene glycol succinate" comprises vitamin E polyethylene glycol succinate (such as D-α-tocopherol polyethylene glycol 1000 succinate, TPGS, one nonionic surfactant (HLB=16-18)) and various ester and ether derivatives of vitamin E polyethylene glycol.

The surfactant is comprised in the emulsion or microemulsion preparation in an amount in the range of about 1 wt % to about 10 wt %, preferably 2 wt % to 6 wt %, more preferably 4 wt % to 5 wt %.

The cosolvent is comprised in the emulsion or microemulsion preparation in an amount in the range of 0 wt % to 20 wt %.

In another aspect, the present invention also provides micelle preparations of the fat-soluble anti-cancer pharmaceutical compounds, comprising the anti-cancer pharmaceutical compounds of the present invention, one or more surfactants, one or more cosolvents and an aqueous phase.

The fat-soluble anti-cancer pharmaceutical compound is comprised in the micelle preparation in an amount in the range of about 0.005 wt % to about 3.0 wt %, preferably about 0.01 wt % to about 2.5 wt %, more preferably about 0.1 wt % to about 1.0 wt %.

The suitable surfactant is comprised in the micelle preparation of the present invention in an amount in the range of about 1 wt % to 10 wt %, preferably 2 wt % to 6 wt %, more preferably 4 wt % to 5 wt %.

The micelle preparation further comprises other ingredients, such as a cosolvent as mentioned above. In one example, the micelle preparation comprises polyethylene glycol and lower alkyl alcohol (such as ethanol). In the micelle preparation, the cosolvent is comprised in the preparation in an amount in the range of about 2 wt % to about 20 wt %.

The emulsion, microemulsion and micelle preparations all comprise an aqueous phase. In one example, the aqueous phase comprises a deionized water. In another example, the aqueous phase comprises a physiological saline. In another example, the aqueous phase comprises an organic acid (such as succinic acid, citric acid) buffer solution.

The present invention also provides a use of the novel pharmaceutical compounds, i.e. a use of the trolox derivative-modified fat-soluble anti-cancer pharmaceutical compounds in the manufacture of an anti-cancer medicament.

For example, the pharmaceutical compounds of the present invention are used to prepare a medicament for treating cancers. The pharmaceutical compounds of the present invention are used to treat blood-system cancers, such as leukemia, lymphoma, myeloma; and non-blood cancers, such as solid tumors (e.g. breast cancer, ovarian cancer, pancreatic cancer, colon cancer, rectal cancer, non-small cell lung cancer, and bladder cancer), sarcomas and gliomas, and the like.

The efficacy and toxicity of the pharmaceutical compounds of the present invention can be determined by in vitro cell or in vivo animal experiments, e.g., ED50 (50% effective dose, the median effective dose: the dose required to achieve a positive response in 50% of the subject population), LD50 (50% lethal dose, the median lethal dose, the dose required to achieve 50% mortality of the subject population) and GI50 (the concentration of an anti-cancer drug that inhibits the growth of cancer cells by 50%). A ratio of median lethal dose (LD50)/median effective dose (ED50) is usually called as a therapeutic index to indicate the safety of a drug. A drug having a greater therapeutic index is safer than one having a lower therapeutic index.

The novel anti-cancer pharmaceutical compounds of the present invention are intended to improve the therapeutic index and pharmaceutical safety, and moreover improve the therapeutic efficacy. A dosage determined from in vitro cell experiments and in vivo animal experiments can be used to establish a dosage range for a human being. Such dosage range preferably falls within the ED50 range which has little or even no toxicity. The dosage usually varies depending on the dosage form(s) being employed, the susceptibility of a patient, administration routes and the like. A conventional dosage of the same or similar drug, such as topotecan or irinotecan, can be usually used as a reference. For example, the conventional dosage of topotecan is 0.2-1.5 mg/kg, and the conventional dosage of irinotecan is 100-350 mg/kg.

The pharmaceutical compounds of the present invention can be used alone or in combination with one or more other therapeutic agents. For example, in the case of the treatment of a cancer, these pharmaceutical compounds can be used in combination with the following therapeutic agents, including, but not limited to: androgen inhibitors, such as flutamide and luprolide; antiestrogens, such as tamoxifen; antimetabolites and cytotoxic drugs, such as daunorubicin, fluorouracil, floxuridine, interferon alpha, methotrexate, plicamycin, mercaptopurine, thioguanine, adriamycin, carmustine, lomustine, cytarabine, cyclophosphamide, doxorubicin, estramustine, altretamine, hydroxyurea, ifosfamide, procarbazine, mutamycin, busulfan, mitoxantrone, carboplatin, cisplatin, streptozocin, bleomycin, dactinomycin, and idamycin; hormones, such as medroxyprogesterone, ethinyl estradiol, estradiol, leuprolide, megestrol, octreotide, diethylstilbestrol, chlorotrianisene, etoposide, podophyllotoxin, and goserelin; mustargen derivatives, such as melphalan, chlorambucil and thiotepa; steroids, such as betamethasone; and other anti-tumor drugs, such as live *Mycobacterium bovis*, dicarbazine, asparaginase, leucovorin, mitotane, vincristine, vinblastine, and taxotere; and the like.

According to the present invention, the pharmaceutical compound molecules having anti-cancer activity, camptothecin or camptothecin derivatives, are covalently bonded to the lipophilic trolox esters or amides by the linking groups to obtain the trolox derivative-modified fat-soluble anti-cancer pharmaceutical compounds, which comprise the anti-cancer pharmaceutically active moieties and the lipophilic moieties and are soluble in a biocompatible lipophilic solvent. The novel anti-cancer pharmaceutical compounds of the present invention have higher anti-cancer activity, and meanwhile better solubility and stability, thereby improving the duration of action (half-life) and efficacy of camptothecin or its derivatives under in vivo physiological conditions and decreasing the toxic and side effects thereof. The pharmaceutical compounds can be formulated into the emulsion and micelle preparations, and therefore widely applied in the treatment of blood system cancers and non-blood system cancers. According to the present invention, various camptothecins and their derivatives can be modified to broaden the application fields thereof, thereby providing a novel method and approach for the clinic application of camptothecins and their derivatives.

The present invention will be described in greater detail in conjunction with the following specific examples. However, it should be understood that the scope of the present invention shall not be limited to the specific embodiments, but shall be defined by the claims.

SPECIFIC EMBODIMENTS

Figure 1:
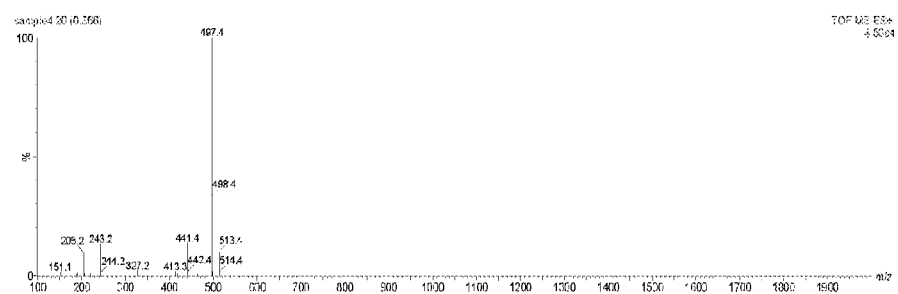
FIG. 1 is a mass spectrum of R-(+)-6-hydroxy-2,5,7,8-tetramethyl chroman-2-carboxylic acid hexadecyl ester.

The following examples illustrate the syntheses, preparations and in vitro cell experiments of the novel anti-cancer pharmaceutical compounds of the present invention. All the examples only contribute to the understandings and implementation of the present invention, and do not constitute any limitation to the present invention.

Example 1

Synthesis of 7-ethyl-10-hydroxycamptothecin R-(+)-6-hydroxy-2,5,7,8-tetramethylchroman-2-carboxylic acid hexadecyl ester-6-succinate The synthesis of said fat-soluble anti-cancer pharmaceutical compound comprises the following steps.

1) Synthesis of R-(+)-6-hydroxy-2,5,7,8-tetramethylchroman-2-carboxylic acid hexadecyl ester The reaction scheme is shown as follows:

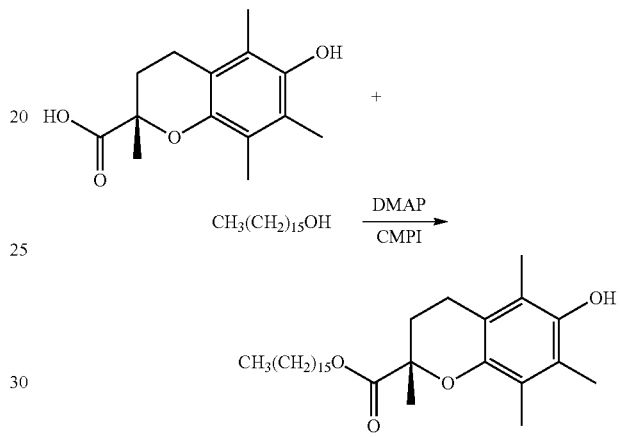

Procedure:

Under electromagnetic stirring, to a 50 mL reaction flask hexadecanol (727 mg, 3 mmol), 4-dimethylaminopyridine (733 mg, 6 mmol), 2-chloro-1-methylpyridinium iodide (766 mg, 3 mmol) and N,N-dimethylformamide (15 mL) were added, and then to the reaction solution a solution of R-(+)-6-hydroxy-2,5,7,8-tetramethylchroman-2-carboxylic acid (750 mg, 3 mmol) in N,N-dimethylformamide (10 mL) was slowly dropwise added. The reaction mixture was reacted for 12 h at room temperature under the protection of nitrogen gas and electromagnetic stirring. The solvent (N,N-dimethylformamide) was removed by a rotary evaporator, and to the residue diethyl ether (50 mL) was added. The resulting mixture was stirred for 2 h, and the precipitate was removed by filtration. The filtrate was concentrated to 10 mL, and then isolated by column chromatography (the stationary phase was 230-400 mesh silica gel, and the eluent was hexane:ethyl acetate (by volume)=10:1), to obtain R-(+)-6-hydroxy-2,5,7,8-tetramethylchroman-2-carboxylic acid hexadecyl ester (1026 mg, yield 72.0%).

Figure 2:
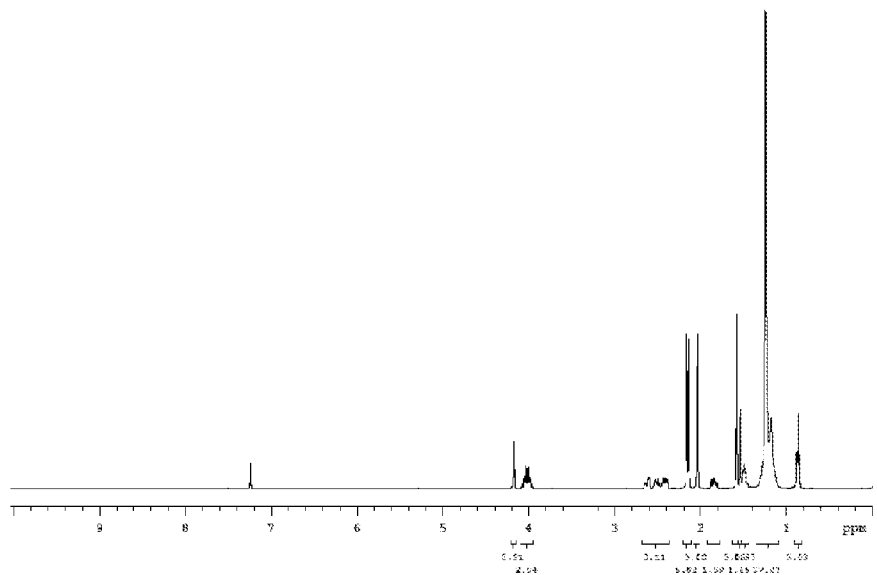
FIG. 2 is a hydrogen nuclear magnetic resonance spectrum of R-(+)-6-hydroxy-2,5,7,8-tetramethylchroman-2-carboxylic acid hexadecyl ester.

The mass spectrum and hydrogen nuclear magnetic resonance spectrum of the resulting compound are shown in FIGS. 1 and 2.

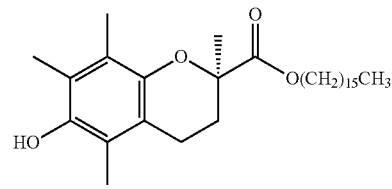

MS (Positive ESI): m/z=475.3 (M+H)+, 497.3 (M+Na)+, 971.6 (2M+Na)+.

$^1$H MR (400 MHz, CDCl$_3$): δ ppm: 4.173 (s, 1H), 4.079-3.690 (m, 2H), 2.648-2.384 (m,3H), 2.161 (s, 3H), 2.136 (s, 3H), 2.038 (s, 3H), 1.879-1.802 (m, 1H), 1.577 (s, 3H), 1.538-1.475 (m, 2H), 1.302-1.176 (m, 26H), 0.880-0.846 (t, J=6.6 Hz, 3H).

2) Synthesis of R-(+)-6-hydroxy-2,5,7,8-tetramethyl-chroman-2-carboxylic acid hexadecyl ester-6-mono-succinate The reaction scheme is shown as follows:

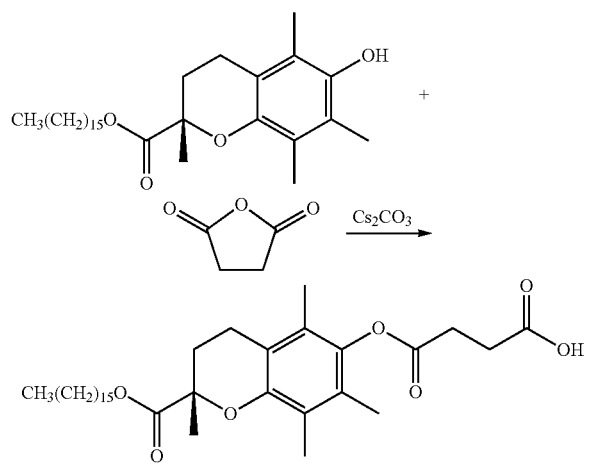

Procedure:

To a 50 mL reaction flask R-(+)-6-hydroxy-2,5,7,8-tetramethylchroman-2-carboxylic acid hexadecyl ester (949 mg, 2 mmol), succinic anhydride (300 mg, 3 mmol), cesium carbonate (815 mg, 2.5 mmol) and N,N-dimethylformamide (20 mL) were added under electromagnetic stirring. The reaction mixture was reacted for 12 h at room temperature under the protection of nitrogen gas and electromagnetic stirring. The reaction solution was then added into ethyl acetate (100 mL) and stirred. The mixed solution was washed with water (50 mL×3) and the organic phase was dried over anhydrous magnesium sulfate. The magnesium sulfate was removed by filtration. The filtrate was then concentrated to 10 mL, and then isolated by column chromatography (the stationary phase was 230-400 mesh silica gel, and the eluent was a mixture of hexane and acetone), to obtain R-(+)-6-hydroxy-2,5,7,8-tetramethylchroman-2-carboxylic acid hexadecyl ester-6-monosuccinate (908 mg, yield 79.0%).

Figure 3:
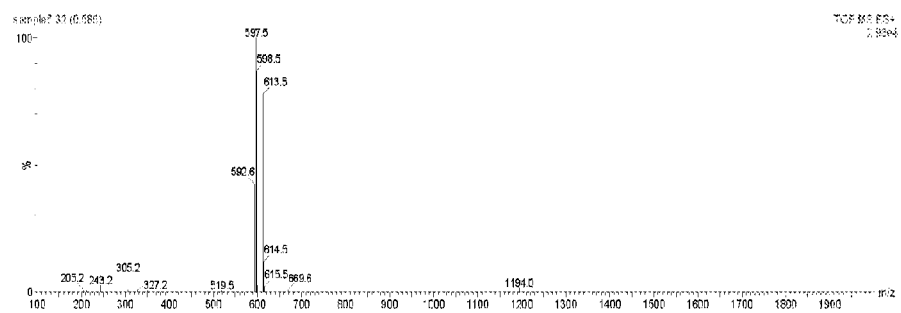
FIG. 3 is a mass spectrum of R-(+)-6-hydroxy-2,5,7,8-tetramethyl chroman-2-carboxylic acid hexadecyl ester-6-monosuccinate.
Figure 4:
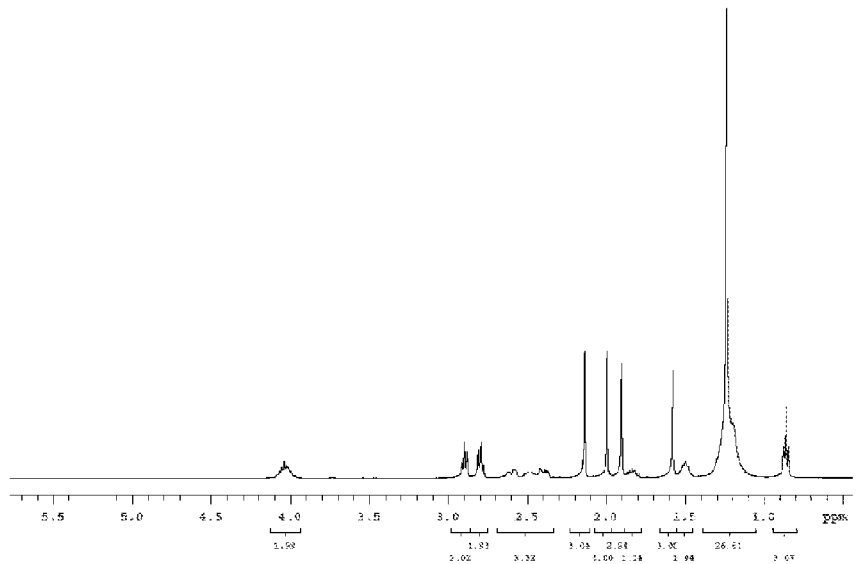
FIG. 4 is a hydrogen nuclear magnetic resonance spectrum of R-(+)-6-hydroxy-2,5,7,8-tetramethylchroman-2-carboxylic acid hexadecyl ester-6-monosuccinate.

The mass spectrum and hydrogen nuclear magnetic resonance spectrum of the synthesized compound are shown in FIGS. 3 and 4.

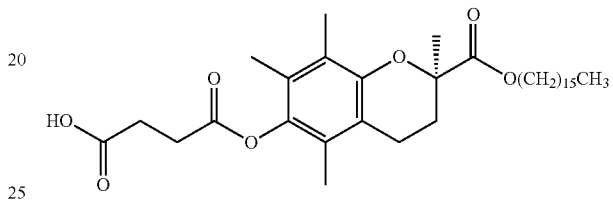

MS (Positive ESI): m/z=597.5 (M+Na)+, 1194.0 (2M+2Na)+.

$^1$H NMR (400 MHz, CDCl$_3$): δ ppm: 4.084-4.002 (m, 2H), 2.911-2.879 (t, J=6.4 Hz, 2H), 2.809-2.776 (t, J=6.6 Hz, 2H), 2.633-2.363 (m, 3H), 2.137 (s, 3H), 1.995 (s, 3H), 1.903 (s, 3H), 1.867-1.791 (m, 1H), 1.580 (s, 3H), 1.514-1.499 (m, 2H), 1.330-1.240 (m, 26H), 0.878-0.844 (t, J=6.8 Hz, 3H).

3) Synthesis of 7-ethyl-10-hydroxycamptothecin R-(+)-6-hydroxy-2,5,7,8-tetramethylchroman-2-carboxylic acid hexadecyl ester-6-succinate The reaction scheme is shown as follows:

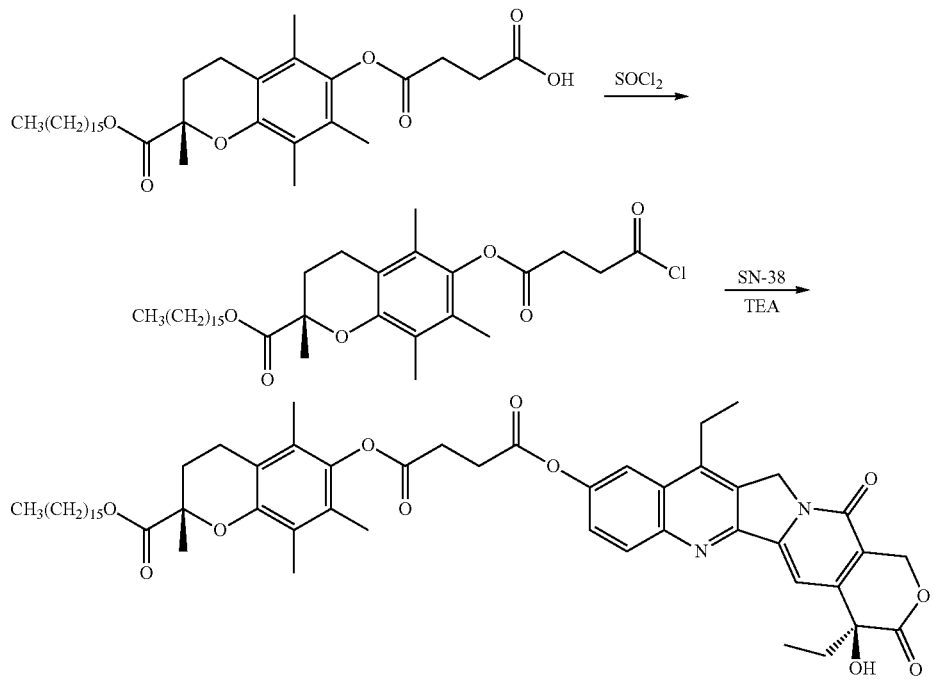

Procedure:

To a 50 mL reaction flask R-(+)-6-hydroxy-2,5,7,8-tetramethylchroman-2-carboxylic acid hexadecyl ester-6-monosuccinate (519 mg, 1 mmol), thionyl chloride (238 mg, 2 mmol), N,N-dimethylformamide (10 µL) and anhydrous toluene (20 mL) were added under electromagnetic stirring. The reaction mixture was reacted for 4 h at room temperature under the protection of nitrogen gas and electromagnetic stirring. Toluene and the excessive amount of thionyl chloride were removed by distillation under reduced pressure to obtain a viscous liquid, and thereto anhydrous chloroform (10 mL) was added, to obtain solution A.

Under stirring, to a 50 mL reaction flask 7-ethyl-10-hydroxycamptothecin (196 mg, 0.5 mmol), anhydrous triethylamine (61 mg, 0.6 mmol) and anhydrous N,N-dimethylacetamide (20 mL) were added, and then thereto the solution A (6 mL) was slowly added. The reaction mixture was reacted for 4 h at room temperature under the protection of nitrogen gas with stirring, and monitored by thin layer chromatography. If there was a small amount of un-reacted 7-ethyl-10-hydroxycamptothecin, suitable amounts of the solution A and triethylamine were additionally added until the reaction was completed. The reaction solution was added into ethyl acetate (100 mL). The mixed solution was washed with water (50 mL×3) and the organic phase was dried over anhydrous magnesium sulfate. The magnesium sulfate was removed by filtration. The filtrate was then concentrated to 10 mL, and then isolated by column chromatography (the stationary phase was 230-400 mesh silica gel, and the eluent was a mixture of hexane and acetone), to obtain 7-ethyl-10-hyroxycamptothecin R-(+)-6-hydroxy-2,5,7,8-tetramethylchroman-2-carboxylic acid hexadecyl ester-6-succinate (340 mg, yield 76.2%).

Figure 5:
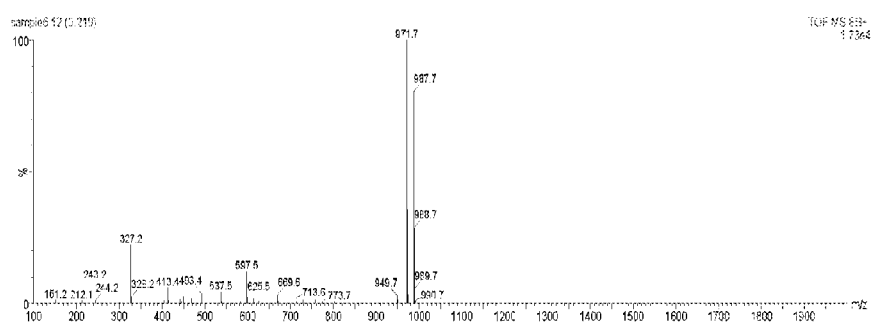
FIG. 5 is a mass spectrum of 7-ethyl-10-hydroxycamptothecin R-(+)-6-hydroxy-2,5,7,8-tetramethylchroman-2-carboxylic acid hexadecyl ester-6-succinate.
Figure 6:
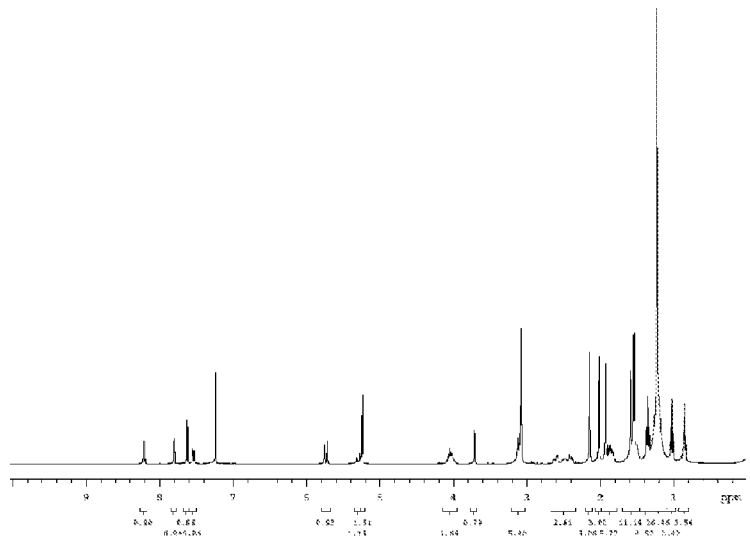
FIG. 6 is a hydrogen nuclear magnetic resonance spectrum of 7-ethyl-10-hydroxycamptothecin R-(+)-6-hydroxy-2,5,7,8-tetramethylchroman-2-carboxylic acid hexadecyl ester-6-succinate.

The mass spectrum and hydrogen nuclear magnetic resonance spectrum of the synthesized compound are shown in FIGS. 5 and 6.

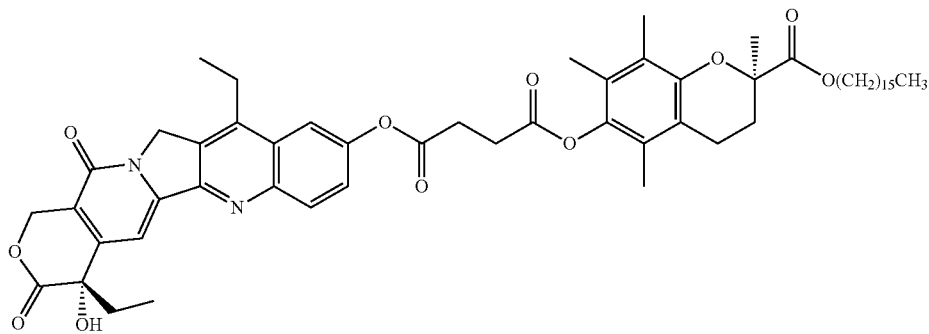

MS(Positive ESI): m/z=949.7(M+H)$^+$, 971.7(M+Na)$^+$.

$^1$H NMR (400 MHz, CDCl$_3$): δ ppm: 8.223-8.200 (d, J=9.2 Hz, 1H), 7.796 (s, 1H), 7.624 (s, 1H), 7.554-7.532 (d, J=8.8 Hz, 1H), 5.757-5.717 (d, J=16 Hz, 1H), 5.312-5.271 (d, J=16.4 Hz, 1H), 5.240 (s, 2H), 4.092-4.021 (m, 2H), 3.714 (s, 1H), 3.142-3.081 (m, 6H), 2.632-2.389 (m, 3H), 2.146 (s, 3H), 2.020 (s, 3H), 1.929 (s, 3H), 1.903-1.802 (m, 1H), 1.589-1.545 (m, 7H), 1.374-1.335 (t, J=7.8 Hz, 3H), 1.229 (m, 26H), 1.042-1.005 (t, J=7.4 Hz, 3H), 0.869-0.836 (t, J=6.6 Hz, 3H).

Example 2

Synthesis of 7-ethyl-10-hydroxycamptothecin R-(+)-6-hydroxy-2,5,7,8-tetramethylchroman-2-carboxylic acid n-hexyl ester-6-succinate The synthesis of said fat-soluble anti-cancer pharmaceutical compound comprises the following step.

1) Synthesis of R-(+)-6-hydroxy-2,5,7,8-tetramethylchroman-2-carboxylic acid n-hexyl ester The reaction scheme is shown as follows:

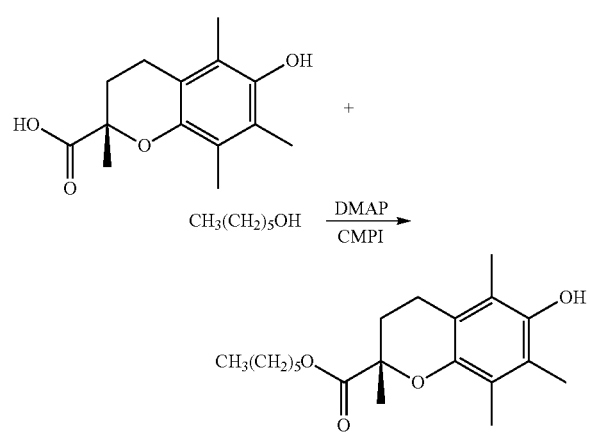

Procedure:

Under electromagnetic stirring, to a 50 mL reaction flask 4-dimethylaminopyridine (978 mg, 8 mmol), 2-chloro-1-methylpyridinium iodide (1022 mg, 4 mmol) and n-hexanol (20 mL) were added, and then to the reaction solution a solution of R-(+)-6-hydroxy-2,5,7,8-tetramethylchroman-2-carboxylate (751 mg, 3 mmol) in N,N-dimethylformamide (10 mL) was slowly dropwise added. The reaction mixture was reacted for 12 h at room temperature under the protection of nitrogen gas and electromagnetic stirring. The solid substances were removed by filtration, and the filtrate was concentrated to 10 mL by a rotary evaporator, and then isolated by column chromatography (the stationary phase was 230-400 mesh silica gel, and the eluent was a mixture of hexane and acetone), to obtain R-(+)-6-hydroxy-2,5,7,8-tetramethylchroman-2-carboxylic acid n-hexyl ester (856 mg, yield 85.0%).

MS(Positive ESI): m/z=335.3(M+H)$^+$, 357.2(M+Na)$^+$, 691.5 (2M+Na)$^+$.

$^1$H MR (400 MHz, CDCl$_3$): δ ppm: 4.081-3.959 (m, 2H), 2.674-2.392 (m, 3H), 2.159 (s, 3H), 2.134 (s, 3H), 1.991 (s, 3H), 1.877-1.737 (m, 1H), 1.578 (s, 3H), 1.534-1.471 (m, 2H), 1.294-1.165 (m, 6H), 0.876-0.839 (t, J=7.4 Hz, 3H).

2) Synthesis of R-(+)-6-hydroxy-2,5,7,8-tetramethyl-chroman-2-carboxylic acid n-hexyl ester-6-monosuccinate The reaction scheme is shown as follows:

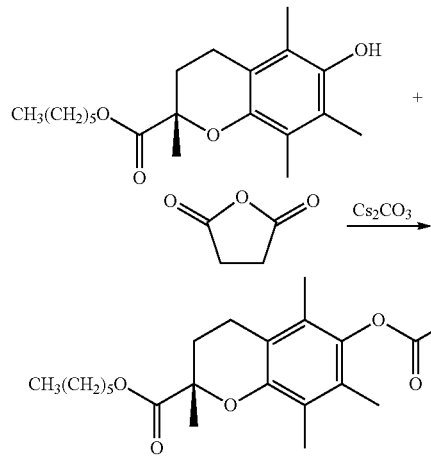

Procedure:

To a 50 mL reaction flask R-(+)-6-hydroxy-2,5,7,8-tetramethylchroman-2-carboxylic acid n-hexyl ester (836 mg, 2.5 mmol), succinic anhydride (300 mg, 3 mmol), cesium carbonate (815 mg, 2.5 mmol) and N,N-dimethylformamide (20 mL) were added under electromagnetic stirring. The reaction mixture was reacted for 12 h at room temperature under the protection of nitrogen gas and electromagnetic stirring. The reaction solution was added into ethyl acetate (100 mL) and stirred. The mixed solution was washed with 0.1N HCl solution (50 mL×3), followed by water (50 mL×3). The organic phase was dried over anhydrous magnesium sulfate. The magnesium sulfate was removed by filtration, and the filtrate was concentrated to 10 mL, and then isolated by column chromatography (the stationary phase was 230-400 mesh silica gel, and the eluent was a mixture of hexane and acetone), to obtain R-(+)-6-hydroxy-2,5,7,8-tetramethyl-chroman-2-carboxylic acid n-hexyl ester-6-monosuccinate (865 mg, yield 79.0%).

MS(Positive ESI): m/z=457.3 (M+Na)$^+$, 891.6(2M+Na)$^+$.

$^1$H NMR (400 MHz, CDCl$_3$): δ ppm: 4.086-3.974 (m, 2H), 2.915-2.883 (t, J=6.4 Hz, 2H), 2.809-2.777 (t, J=6.4 Hz, 2H), 2.667-2.373 (m, 3H), 2.135 (s, 3H), 1.992 (s, 3H), 1.901 (s, 3H), 1.864-1.788 (m, 1H), 1.580 (s, 3H), 1.491 (s, 2H), 1.281-1.189 (m, 6H), 0.857-0.822 (t, J=7 Hz, 3H).

3) Synthesis of 7-ethyl-10-hydroxycamptothecin R-(+)-6-hydroxy-2,5,7,8-tetramethylchroman-2-carboxylic acid n-hexyl ester-6-succinate The reaction scheme is shown as follows

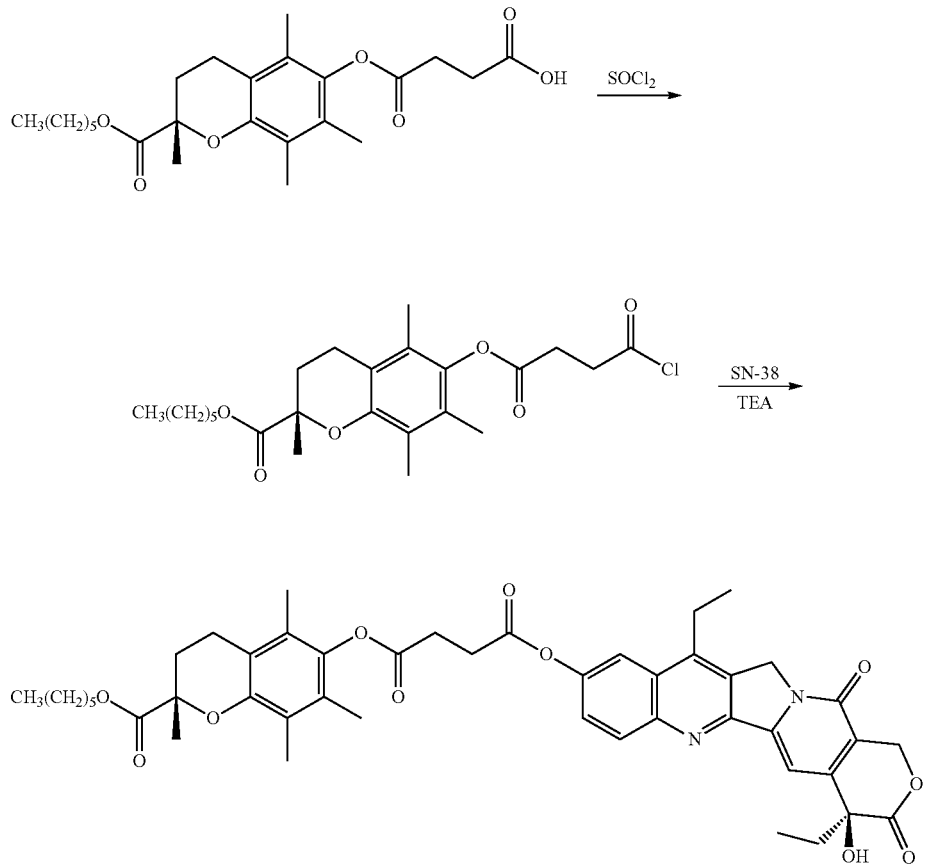

35

Procedure:

To a 50 mL reaction flask R-(+)-6-hydroxy-2,5,7,8-tetramethylchroman-2-carboxylic acid n-hexyl ester-6-monosuccinate (439 mg, 1 mmol), thionyl chloride (238 mg, 2 mmol), N,N-dimethylformamide (10 μL) and anhydrous toluene (20 mL) were added under electromagnetic stirring. The reaction mixture was reacted for 4 h at room temperature under the protection of nitrogen gas and electromagnetic stirring. Toluene and an excessive amount of thionyl chloride were removed by distillation under reduced pressure to obtain a viscous liquid, and thereto anhydrous chloroform (10 mL) was added to obtain solution A.

Under stirring, to a 50 mL reaction flask 7-ethyl-10-hyroxycamptothecin (196 mg, 0.5 mmol), anhydrous triethylamine (61 mg, 0.6 mmol) and anhydrous N,N-dimethylacetamide (20 mL) were added, and then thereto the solution A (6 mL) was slowly added. The reaction mixture was reacted for 4 h at room temperature under the protection of nitrogen gas with stirring and monitored by thin layer chromatography. If there was a small amount of un-reacted 7-ethyl-10-hydroxycamptothecin, suitable amounts of the solution A and triethylamine were additionally added until the reaction was completed. The reaction solution was added into ethyl acetate (100 mL). The mixed solution was washed with water (50 mL×3) and the organic phase was dried over anhydrous magnesium sulfate. The magnesium sulfate was removed by filtration, and the filtrate was concentrated to 10 mL, and then isolated by column chromatography (the stationary phase was 230-400 mesh silica gel, and the eluent was a mixture of hexane and acetone), to obtain 7-ethyl-10-hyroxycamptothecin R-(+)-6-hydroxy-2,5,7,8-tetramethylchroman-2-carboxylic acid n-hexyl ester-6-succinate (358 mg, yield 90.0%).

Figure 7:
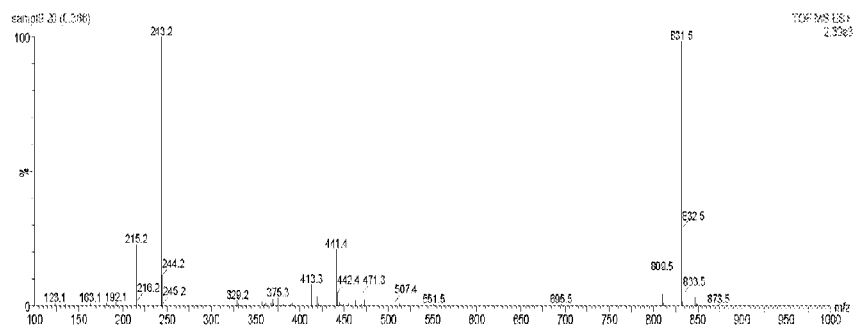
FIG. 7 is a mass spectrum of 7-ethyl-10-hydroxycamptothecin R-(+)-6-hydroxy-2,5,7,8-tetramethylchroman-2-carboxylic acid n-hexyl ester-6-succinate.
Figure 8:
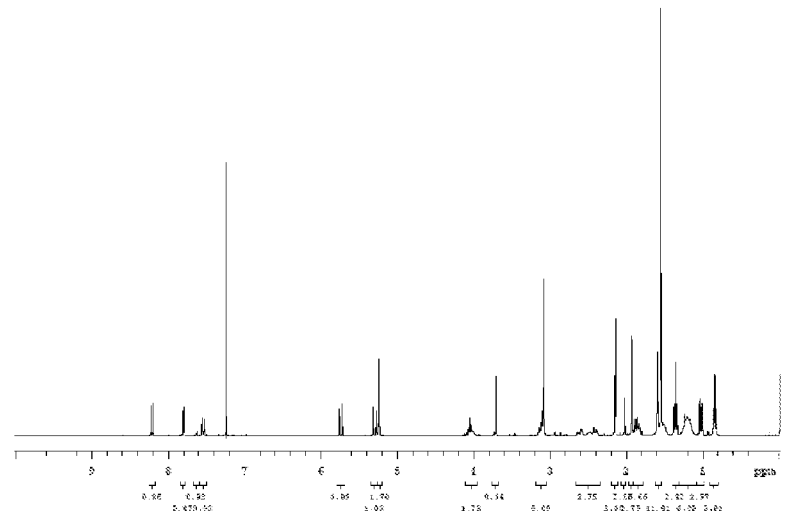
FIG. 8 is a hydrogen nuclear magnetic resonance spectrum of 7-ethyl-10-hydroxycamptothecin R-(+)-6-hydroxy-2,5,7,8-tetramethylchroman-2-carboxylic acid n-hexyl ester-6-succinate.

The mass spectrum and hydrogen nuclear magnetic resonance spectrum of the synthesized fat-soluble anti-cancer pharmaceutical compound are shown in FIGS. 7 and 8.

36

Example 3

Synthesis of 7-ethyl-10-hydroxycamptothecin R-(+)-6-hydroxy-2,5,7,8-tetramethylchroman-2-carboxylic acid dodecyl ester-6-succinate The synthesis of said fat-soluble anti-cancer pharmaceutical compound comprises the following step.

1) Synthesis of R-(+)-6-hydroxy-2,5,7,8-tetramethylchroman-2-carboxylic acid dodecyl ester The reaction scheme is shown as follows:

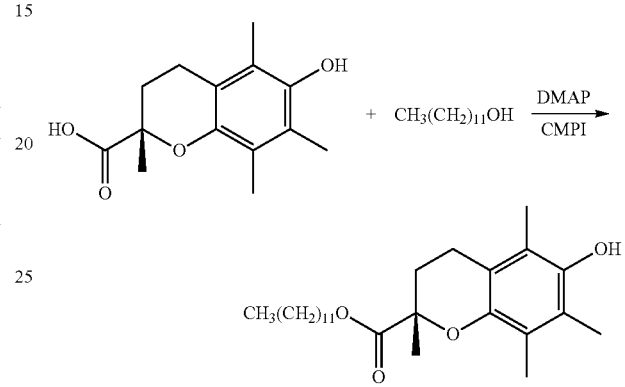

Procedure:

Under electromagnetic stirring, to a 50 mL reaction flask dodecanol (373 mg, 2 mmol), 4-dimethylaminopyridine (489 mg, 4 mmol), 2-chloro-1-methylpyridinium iodide (511 mg, 2 mmol) and N,N-dimethylformamide (10 mL) were added, and then to the reaction solution a solution of R-(+)-6-hydroxy-2,5,7,8-tetramethylchroman-2-carboxylic acid (500 mg, 2 mmol) in N,N-dimethylformamide (10 mL) was slowly dropwise added. The reaction mixture was reacted for 12 h at

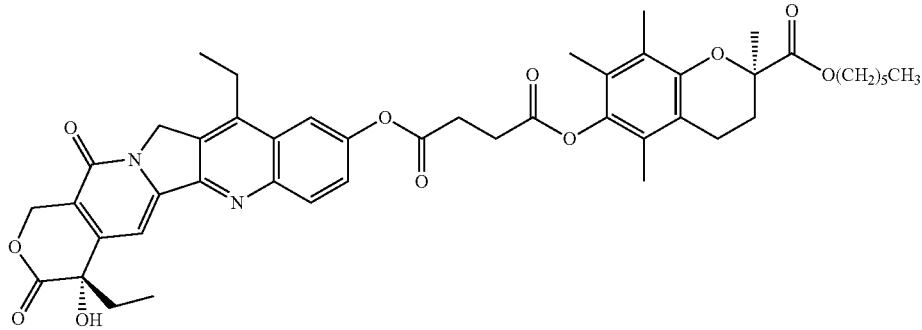

MS(Positive ESI): m/z=809.5(M+H)$^+$, 831.5(M+Na)$^+$.

$^1$H NMR (400 MHz, CDCl$_3$) δ ppm: 8.223-8.200 (d, J=9.2 Hz, 1H), 7.795 (s, 1H), 7.625 (s, 1H), 7.555-7.532 (d, J=9.2 Hz, 1H), 5.759-5.718 (d, J=16.4 Hz, 1H), 5.313-5.273 (d, J=16 Hz, 1H), 5.241 (s, 2H), 4.066-4.020 (m, 2H), 3.705 (s, 1H), 3.142-3.083 (6H), 2.632-2.382 (m, 3H), 2.144 (s, 3H), 2.018 (s, 3H), 1.927 (s, 3H), 1.901-1.799 (m, 1H), 1.590-1.512 (m, 7H), 1.372-1.334 (t, J=7.6 Hz, 3H), 1.232-1.170 (m, 6H), 1.041-1.005 (t, J=7.2 Hz, 3H), 0.857-0.822 (t, J=7 Hz, 3H).

room temperature under the protection of nitrogen gas and electromagnetic stirring. The solid substances were removed by filtration, and the filtrate was concentrated to 10 mL by a rotary evaporator, was and then isolated by column chromatography (the stationary phase was 230-400 mesh silica gel, and the eluent was a mixture of hexane and ethyl acetate), to obtain R-(+)-6-hydroxy-2,5,7,8-tetramethylchroman-2-carboxylic acid dodecyl ester (365 mg, yield 43.6%).

MS(Positive ESI): m/z=419.4(M+H)$^+$, 441.4(M+Na)$^+$, 859.7(2M+Na)$^+$.

$^1$H MR (400 MHz, CDCl$_3$): δ ppm: 4.183 (s, 1H), 4.079-3.961 (m, 2H), 2.655-2.383 (m, 3H), 2.161 (s, 3H), 2.135 (s, 3H), 2.037 (s, 3H), 1.879-1.803 (m, 1H), 1.578 (s, 3H), 1.525-1.459 (m, 2H), 1.304-1.178 (m, 18H), 0.884-0.849 (t, J=7.0 Hz, 3H).

2) Synthesis of R-(+)-6-hydroxy-2,5,7,8-tetramethyl-chroman-2-carboxylic acid dodecyl ester-6-mono-succinate The reaction scheme is shown as follows

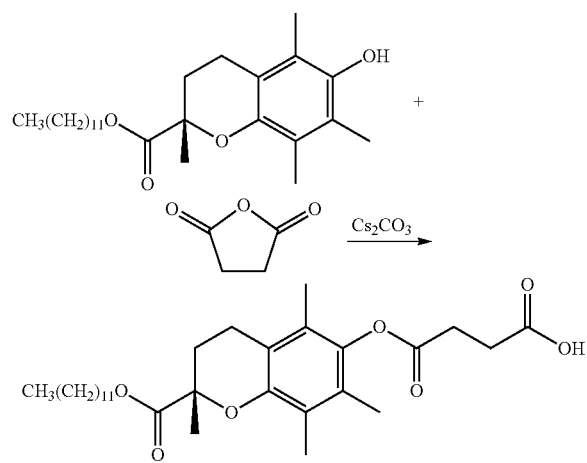

Procedure:

To a 50 mL reaction flask R-(+)-6-hydroxy-2,5,7,8-tetramethylchroman-2-carboxylic acid dodecyl ester (837 mg, 2 mmol), succinic anhydride (300 mg, 3 mmol), cesium carbonate (815 mg, 2.5 mmol) and N,N-dimethylformamide (20 mL) were added under electromagnetic stirring. The reaction mixture was reacted for 12 h at room temperature under the protection of nitrogen gas and electromagnetic stirring. The reaction solution was added into ethyl acetate (100 mL) and stirred. The mixed solution was washed with 0.1N HCl solution (50 mL×3), followed by water (50 mL×3). The organic phase was dried over anhydrous magnesium sulfate. The magnesium sulfate was removed by filtration, and the filtrate was concentrated to 10 mL, and then isolated by column chromatography (the stationary phase was 230-400 mesh silica gel, and the eluent was a mixture of hexane and acetone), to obtain R-(+)-6-hydroxy-2,5,7,8-tetramethylchroman-2-carboxylic acid dodecyl ester-6-monosuccinate (908 mg, yield 86.0%).

MS(Positive ESI): m/z=541.4(M+Na)+.

$^1$H NMR (400 MHz, CDCl$_3$): δ ppm: 4.089-3.999 (m, 2H), 2.911-2.879 (t, J=6.4 Hz, 2H), 2.807-2.774 (t, J=6.6 Hz, 2H), 2.664-2.363 (m, 3H), 2.136 (s, 3H), 1.994 (s, 3H), 1.902 (s, 3H), 1.866-1.790 (m, 1H), 1.579 (s, 3H), 1.496 (m, 2H), 1.299-1.192 (m, 18H), 0.878-0.844 (t, J=6.8 Hz, 3H).

3) Synthesis of 7-ethyl-10-hydroxycamptothecin R-(+)-6-hydroxy-2,5,7,8-tetramethylchroman-2-carboxylic acid dodecyl ester-6-succinate The reaction scheme is shown as follows

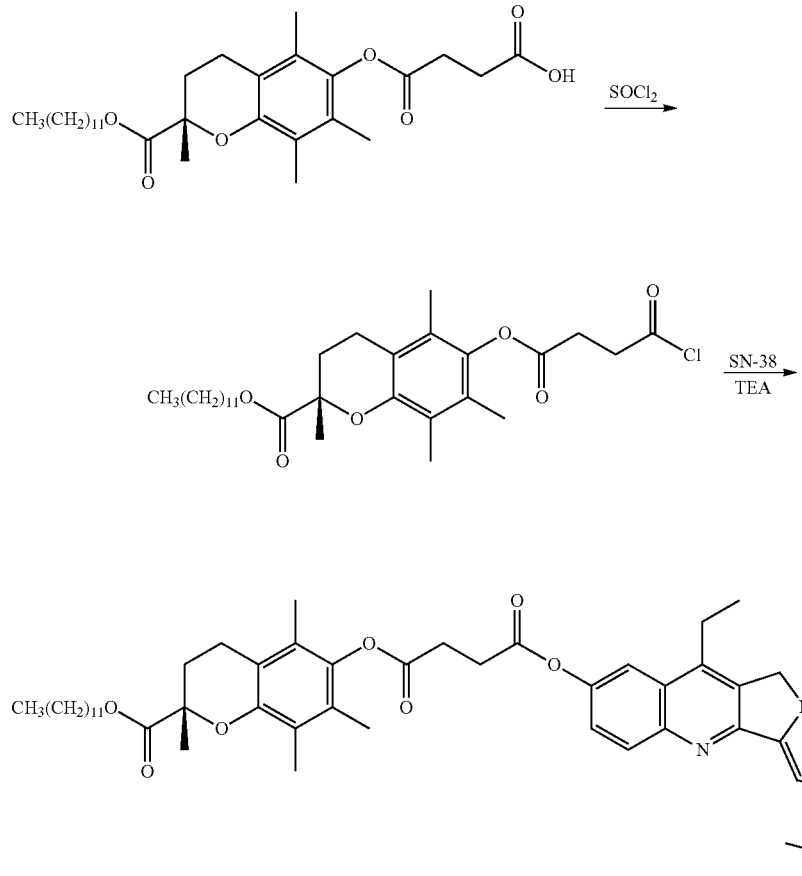

Procedure:

To a 50 mL reaction flask R-(+)-6-hydroxy-2,5,7,8-tetramethylchroman-2-carboxylic acid dodecyl ester-6-monosuccinate (519 mg, 1 mmol), thionyl chloride (238 mg, 2 mmol), N,N-dimethylformamide (10 μL) and anhydrous toluene (20 mL) were added under electromagnetic stirring. The reaction mixture was reacted for 4 h at room temperature under the protection of nitrogen gas and electromagnetic stirring. Toluene and an excessive amount of thionyl chloride were removed by distillation under reduced pressure to obtain a viscous liquid, and thereto anhydrous chloroform (10 mL) was added to obtain solution A.

Under stirring, to a 50 mL reaction flask 7-ethyl-10-hydroxycamptothecin (196 mg, 0.5 mmol), anhydrous triethylamine (61 mg, 0.6 mmol) and anhydrous N,N-dimethylacetamide (20 mL) were added, and then thereto the solution A (6 mL) was slowly added. The reaction mixture was reacted for 4 h at room temperature under the protection of nitrogen gas with stirring, and monitored by thin layer chromatography. If there was a small amount of un-reacted 7-ethyl-10-hydroxycamptothecin, suitable amounts of the solution A and triethylamine were additionally added until the reaction was completed. The reaction solution was added into ethyl acetate (100 mL). The mixed solution was washed with water (50 mL×3) and the organic phase was dried over anhydrous magnesium sulfate. The magnesium sulfate was removed by filtration, and the filtrate was concentrated to 10 mL, and then isolated by column chromatography (the stationary phase was 230-400 mesh silica gel, and the eluent was a mixture of hexane and acetone), to obtain 7-ethyl-10-hyroxycamptothecin R-(+)-6-hydroxy-2,5,7,8-tetramethylchroman-2-carboxylic acid dodecyl ester-6-succinate (340 mg, yield 76.2%).

Figure 9:
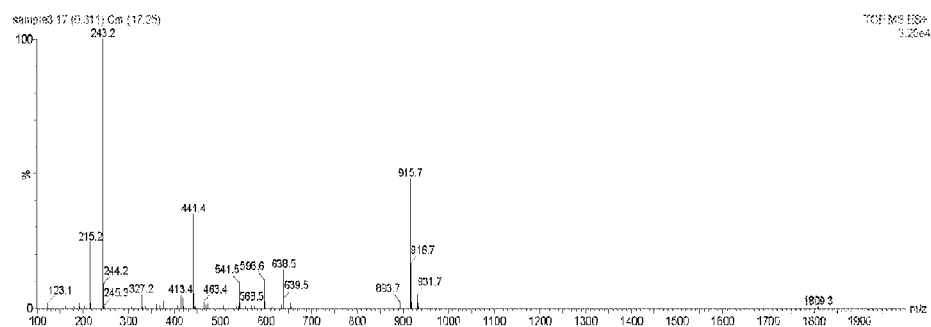
FIG. 9 is a mass spectrum of 7-ethyl-10-hydroxycamptothecin R-(+)-6-hydroxy-2,5,7,8-tetramethylchroman-2-carboxylic acid dodecyl ester-6-succinate.
Figure 10:
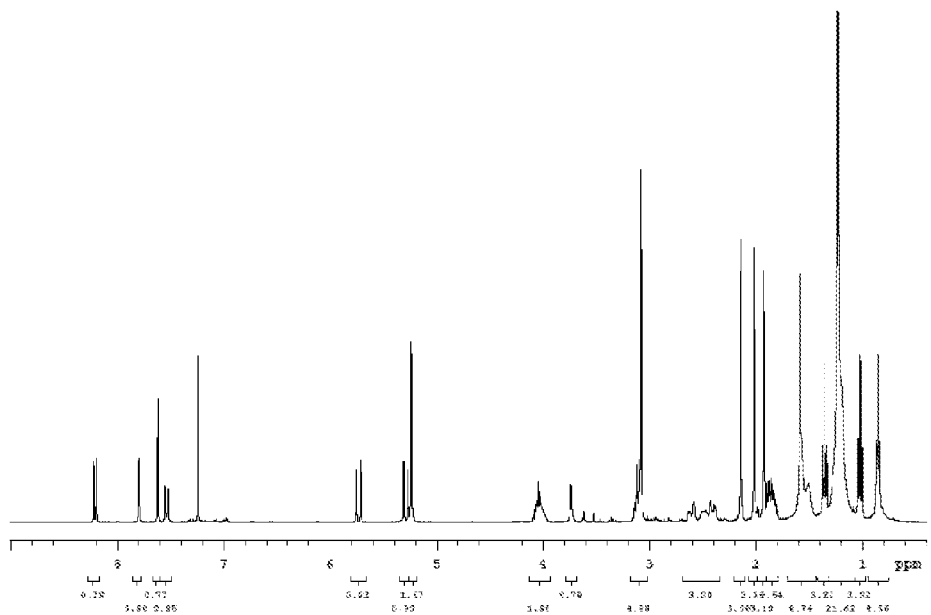
FIG. 10 is a hydrogen nuclear magnetic resonance spectrum of 7-ethyl-10-hydroxycamptothecin R-(+)-6-hydroxy-2,5,7,8-tetramethylchroman-2-carboxylic acid dodecyl ester-6-succinate.

The mass spectrum and hydrogen nuclear magnetic resonance spectrum of the synthesized fat-soluble anti-cancer pharmaceutical compound are shown in FIGS. 9 and 10.

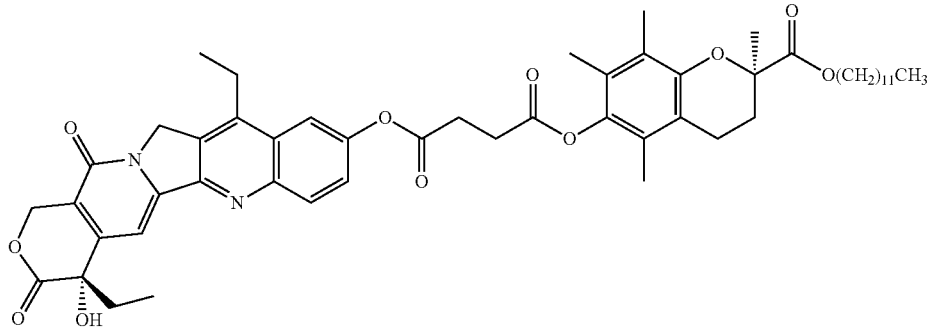

MS(Positive ESI): m/z=893.7(M+H)$^+$, 915.7(M+Na)$^+$.

$^1$H NMR (400 MHz, CDCl$_3$): δ ppm: 8.220-8.197 (d, J=9.2 Hz, 1H), 7.794 (s, 1H), 7.623 (s, 1H), 7.552-7.529 (d, J=9.2 Hz, 1H), 5.755-5.714 (d, J=16.4 Hz, 1H), 5.310-5.269 (d, J=16.4 Hz, 1H), 5.238 (s, 2H), 4.075-4.108 (m, 2H), 3.739 (s, 1H), 3.140-3.081 (m, 6H), 2.633-2.397 (t, 3H), 2.145 (s, 3H), 2.020 (s, 3H), 1.929 (s, 3H), 1.902-1.801 (m, 1H), 1.589-1.506 (s, 7H), 1.373-1.335 (t, J=7.6 Hz, 3H), 1.272-1.223 (m, 18), 1.041-1.004 (t, J=7.4 Hz, 3H), 0.869-0.835 (t, J=6.8 Hz, 3H).

Example 4

Synthesis of 7-ethyl-10-hydroxycamptothecin (±)-6-hydroxy-2,5,7,8-tetramethylchroman-2-carboxylic acid hexadecyl ester-6-succinate The synthesis of said fat-soluble anti-cancer pharmaceutical compound comprises the following step.

1) Synthesis of (±)-6-hydroxy-2,5,7,8-tetramethylchroman-2-carboxylic acid hexadecyl ester The reaction scheme is shown as follows:

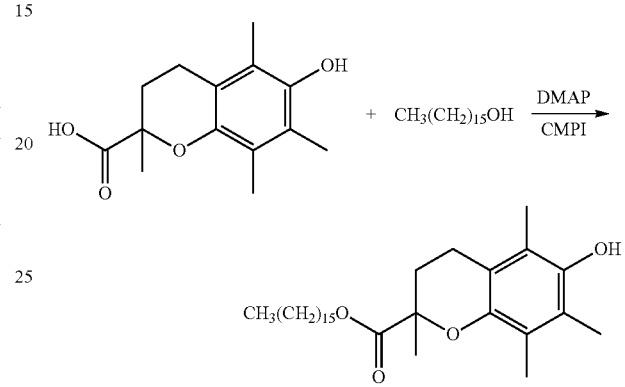

Procedure:

Under electromagnetic stirring, to a 100 mL reaction flask hexadecanol (970 mg, 4 mmol), 4-dimethylaminopyridine (1466 mg, 12 mmo), 2-chloro-1-methylpyridinium iodide (1533 mg, 6 mmol) and dioxane (20 mL) were added, and then to the reaction solution a solution of (±)-6-hydroxy-2,5,7,8-tetramethylchroman-2-carboxylic acid (1001 mg, 4 mmol) in dioxane (20 mL) was slowly dropwise added. The reaction mixture was reacted for 12 h at room temperature under the protection of nitrogen gas and electromagnetic stirring. The solvent (dioxane) was removed by a rotary evaporator, and thereto diethyl ether (50 mL) was added. The resulting mixture was stirred for 2 h, and the precipitate was removed by filtration. The filtrate was concentrated to 10 mL, and isolated by column chromatography (the stationary phase was 230-400 mesh silica gel, the eluent was hexane:ethyl acetate=10:1), to obtain (±)-6-hydroxy-2,5,7,8-tetramethylchroman-2-carboxylic acid hexadecyl ester (1242 mg, yield 65.4%).

MS(Positive ESI): m/z=475.3(M+H)+, 497.3(M+Na)+, 971.5(2M+Na)+.

$^1$H NMR (400 MHz, CDCl$_3$) δ ppm: 4.167 (s, 1H), 4.077-3.974 (m, 2H), 2.647-2.383 (m, 3H), 2.160 (s, 3H), 2.135 (s, 3H), 2.037 (s, 3H), 1.878-1.801 (m, 1H), 1.577 (s, 3H), 1.535-1.471 (m, 2H), 1.282-1.174 (m, 26H), 0.879-0.844 (t, J=7.0 Hz, 3H).

2) Synthesis of (±)-6-hydroxy-2,5,7,8-tetramethyl-chroman-2-carboxylic acid hexadecyl ester-6-mono-succinate The reaction scheme is shown as follows:

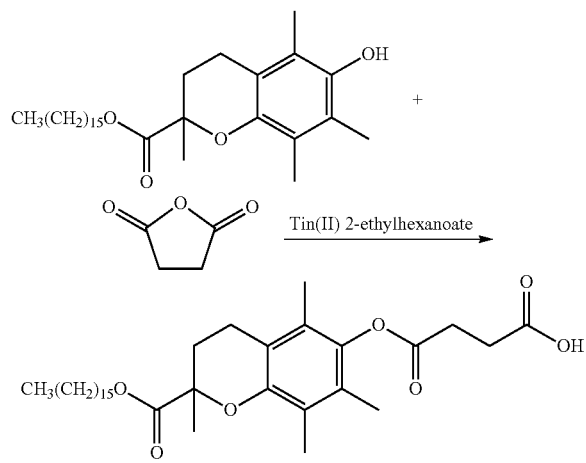

Procedure:

To a 100 mL reaction flask (±)-6-hydroxy-2,5,7,8-tetramethylchroman-2-carboxylic acid hexadecyl ester (949 mg, 2 mmol), succinic anhydride (300 mg, 3 mmol), tin (II) 2-ethylhexanoate (100 µg) and anhydrous xylene (50 mL) were added. The reaction mixture was heated and refluxed for 8 h under the protection of nitrogen gas. The solid substances were removed by filtration, and the solvent (xylene) was removed by a rotary evaporator. The residue was isolated by column chromatography (the stationary phase was 230-400 mesh silica gel, and the eluent was a mixture of hexane and acetone), to obtain (±)-6-hydroxy-2,5,7,8-tetramethylchroman-2-carboxylic acid hexadecyl ester-6-monosuccinate (1002 mg, yield 87.2%).

MS(Positive ESI): m/z=597.3(M+Na)+.

$^1$H NMR (400 MHz, CDCl$_3$): δ ppm: 4.066-3.999 (m, 2H), 2.916-2.884 (t, J=6.4 Hz, 2H), 2.811-2.778 (t, J=6.6 Hz, 2H), 2.625-2.363 (m, 3H), 2.136 (s, 3H), 1.994 (s, 3H), 1.903 (s, 3H): 1.866-1.790 (m, 1H), 1.579 (s, 3H), 1.512-1.496 (m, 2H), 1.298-1.193 (m, 26H), 0.876-0.842 (t, J=6.8 Hz, 3H).

3) Synthesis of 7-ethyl-10-hydroxycamptothecin (±)-6-hydroxy-2,5,7,8-tetramethylchroman-2-carboxylic acid hexadecyl ester-6-succinate The reaction scheme is shown as follows

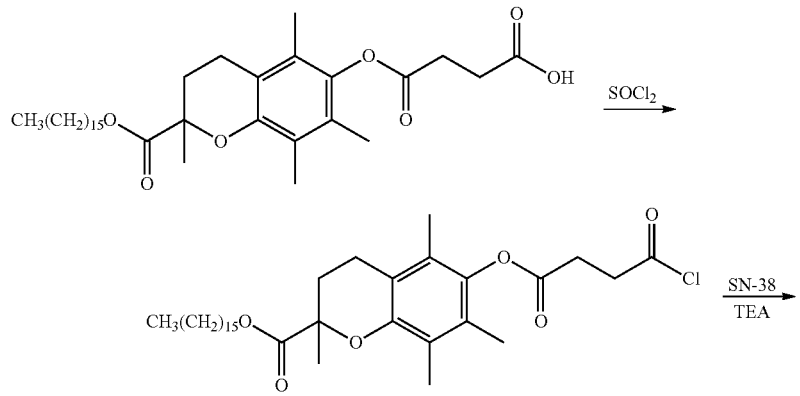

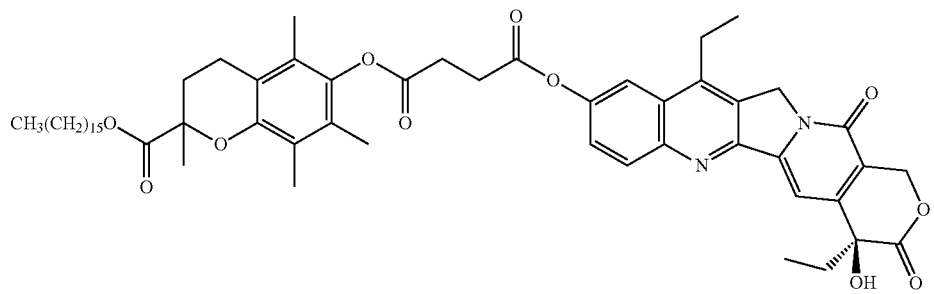

Procedure:

To a 50 mL reaction flask (±)-6-hydroxy-2,5,7,8-tetramethylchroman-2-carboxylic acid hexadecyl ester-6-monosuccinate (862 mg, 1.5 mmol), thionyl chloride (357 mg, 3 mmol), N,N-dimethylformamide (10 μL) and anhydrous toluene (30 mL) were added under electromagnetic stirring. The reaction mixture was reacted for 4 h at room temperature under the protection of nitrogen gas and electromagnetic stirring. Toluene and an excessive amount of thionyl chloride were removed by distillation under reduced pressure to obtain a viscous liquid, and thereto anhydrous chloroform (10 mL) was added to obtain solution A.

Under stirring, to a 50 mL reaction flask 7-ethyl-10-hyroxycamptothecin (392 mg, 1 mmol), anhydrous triethylamine (121 mg, 1.2 mmol) and anhydrous N,N-dimethylacetamide (20 mL) were added, and then thereto the solution A (6 mL) was slowly added. The reaction mixture was reacted for 4 h at room temperature under the protection of nitrogen gas with stirring, and monitored by thin layer chromatography. If there was a small amount of un-reacted 7-ethyl-10-hydroxycamptothecin, suitable amounts of the solution A and triethylamine were additionally added until the reaction was completed. The reaction solution was added into ethyl acetate (100 mL). The mixed solution was washed with water (50 mL×3) and the organic phase was dried over anhydrous magnesium sulfate. The magnesium sulfate was removed by filtration, and the filtrate was concentrated to 10 mL, and then isolated by column chromatography (the stationary phase was 230-400 mesh silica gel, and the eluent was a mixture of hexane and acetone), to obtain 7-ethyl-10-hyroxycamptothecin (±)-6-hydroxy-2,5,7,8-tetramethylchroman-2-carboxylic acid hexadecyl ester-6-succinate (475 mg, yield 50.0%).

Figure 11:
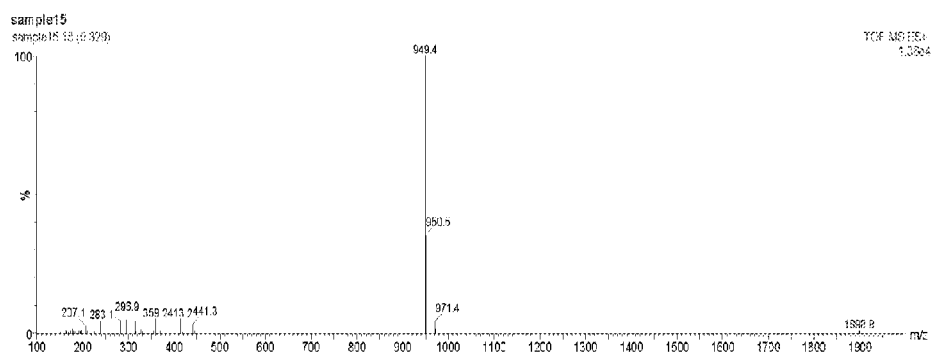
FIG. 11 is a mass spectrum of 7-ethyl-10-hydroxycamptothecin (±)-6-hydroxy-2,5,7,8-tetramethylchroman-2-carboxylic acid hexadecyl ester-6-succinate.
Figure 12:
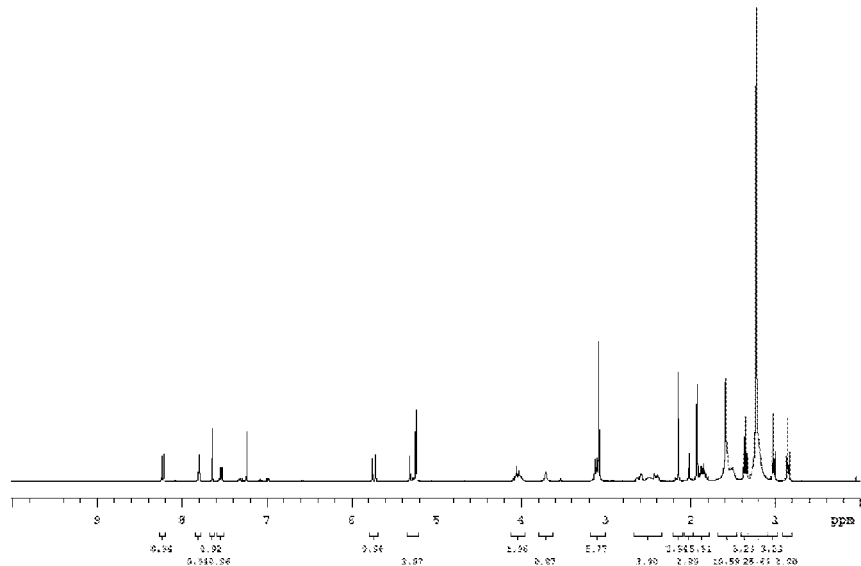
FIG. 12 is a hydrogen nuclear magnetic resonance spectrum of 7-ethyl-10-hydroxycamptothecin (±)-6-hydroxy-2,5,7,8-tetramethylchroman-2-carboxylic acid hexadecyl ester-6-succinate.

The mass spectrum and hydrogen nuclear magnetic resonance spectrum of the synthesized fat-soluble anti-cancer pharmaceutical compound are shown in FIGS. 11 and 12.

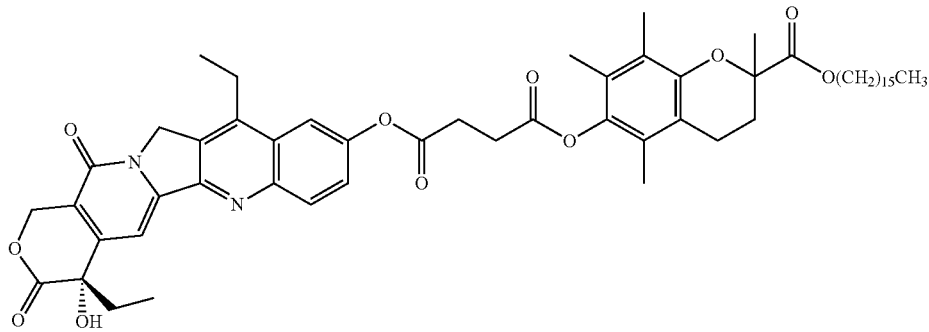

MS(Positive ESI): m/z=949.4(M+H)$^+$,1898.8 (2M+H)$^+$.

$^1$H NMR (400 MHz, CDCl$_3$): δ ppm: 8.238-8.215 (d, J=4.6 Hz, 1H), 7.798 (s, 1H), 7.645 (s, 1H), 7.645-7.529 (m, 1H), 5.758-5.718 (d, J=8 Hz, 1H), 5.313-5.272 (d, J=8 Hz, 1H), 5.243 (s, 2H), 4.075-4.017 (m, 2H), 3.709 (s, 1H), 3.144-3.082 (m, 6H), 2.597-2.382 (m, 3H), 2.145 (s, 3H), 2.020 (s, 3H), 1.928 (s, 3H), 1.902-1.801 (m, 1H), 1.598-1.507 (m, 5H), 1.374-1.336 (t, J=7.6 Hz), 1.289-1.187 (m, 26H), 1.024-1.005 (t, J=7.4 Hz), 0.869-0.835 (t, J=6.8 Hz, 3H).

Example 5

Synthesis of 7-ethyl-10-hydroxycamptothecin N-hexadecylamino R-(+)-6-hydroxy-2,5,7,8-tetramethylchroman-2-carboxamide-6-succinate The synthesis of said fat-soluble anti-cancer pharmaceutical compound comprises the following step:

1) Synthesis of N-hexadecylamino R-(+)-6-hydroxy-2,5,7,8-tetramethyl chroman-2-carboxamide The reaction scheme is shown as follows:

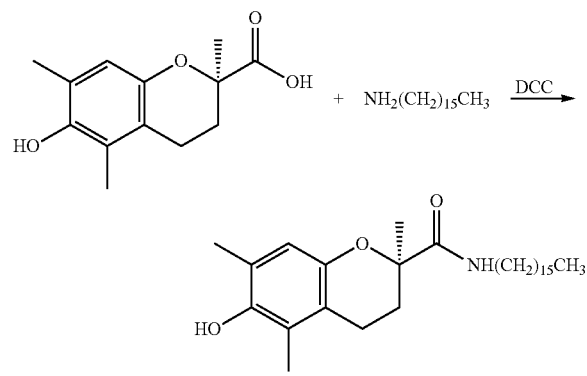

Procedure:

To a 50 mL reaction flask N,N'-dicyclohexylcarbodiimide (DCC, 825 mg, 4 mmol), hexadecylamine (724 mg, 3 mmol), R-(+)-6-hydroxy-2,5,7,8-tetramethylchroman-2-carboxylic acid (751 mg, 3 mmol) and N,N-dimethylformamide (20 mL) were added. Under electromagnetic stirring, the reaction mixture was reacted for 12 h at room temperature under the protection of nitrogen gas. The solid substances were removed by filtration. N,N-dimethylformamide in the filtrate was removed by a rotary evaporator, and thereto ethyl acetate (10 mL) was added. The resulting mixture was stirred and then isolated by column chromatography (the stationary phase was 230-400 mesh silica gel, and the eluent was a mixture of hexane and acetone), to obtain N-hexadecylamino R-(+)-6-hydroxy-2,5,7,8-tetramethylchroman-2-carboxamide (1074 mg, yield 75.6%).

2) Synthesis of N-hexadecylamino R-(+)-6-hydroxy-2,5,7,8-tetramethyl chroman-2-carboxamide-6-monosuccinate The reaction scheme is shown as follows:

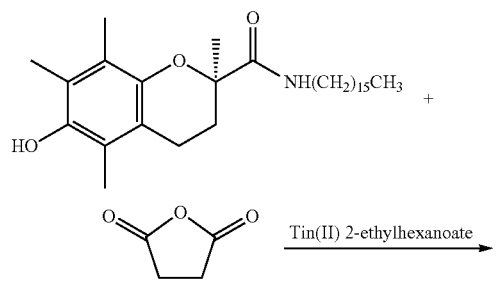

Procedure:

To a 50 mL reaction flask N-hexadecylamino R-(+)-6-hydroxy-2,5,7,8-tetramethylchroman-2-carboxamide (947 mg, 2 mmol), succinic anhydride (300 mg, 3 mmol), tin (II) 2-ethylhexanoate (100 mg) and anhydrous xylene (50 mL) were added. The reaction mixture was heated and refluxed for 8 h under the protection of nitrogen gas, and the solid substances were removed by filtration. The resulting mixture was isolated by column chromatography (the stationary phase was 230-400 mesh silica gel, and the eluent was a mixture of hexane and acetone), to obtain N-hexadecylamino R-(+)-6-hydroxy-2,5,7,8-tetramethylchroman-2-carboxamide-6-monosuccinate (943 mg, yield 82.2%).

3) Synthesis of 7-ethyl-10-hydroxycamptothecin N-hexadecylamino R-(+)-6-hydroxy-2,5,7,8-tetramethylchroman-2-carboxamide-6-succinate The reaction scheme is shown as follows:

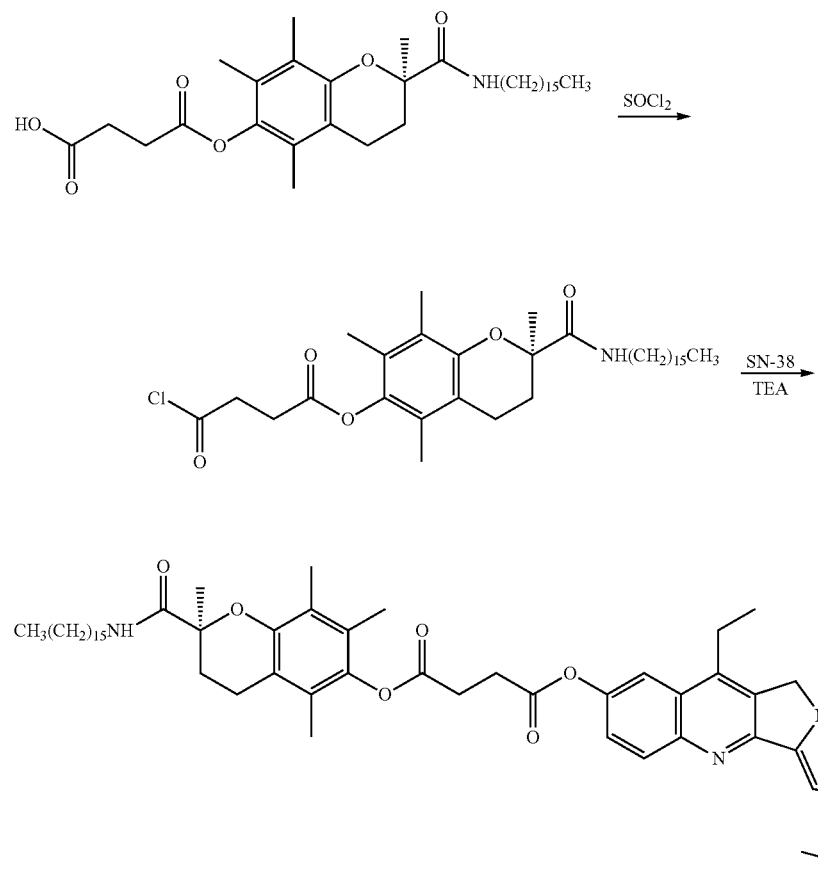

-continued

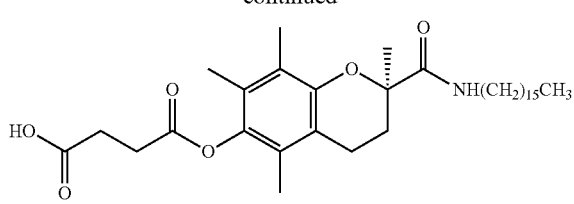

Procedure:

To a 50 mL reaction flask N-hexadecylamino R-(+)-6-hydroxy-2,5,7,8-tetramethylchroman-2-carboxamide-6-monosuccinate (574 mg, 1 mmol), thionyl chloride (238 mg, 2 mmol), N,N-dimethylformamide (10 µL) and anhydrous toluene (20 mL) were added under electromagnetic stirring. The reaction mixture was reacted for 4 h at room temperature under the protection of nitrogen gas and electromagnetic stirring. Toluene and an excessive amount of thionyl chloride were removed by distillation under reduced pressure to obtain a viscous liquid, and thereto anhydrous chloroform (10 mL) was added to obtain solution A.

Under electromagnetic stirring, to a 50 mL reaction flask 7-ethyl-10-hydroxycamptothecin (196 mg, 0.5 mmol), anhydrous triethylamine (61 mg, 0.6 mmol) and anhydrous N,N-dimethylacetamide (20 mL) were added, and then thereto the solution A (6 mL) was slowly added. The reaction mixture was reacted for 4 h at room temperature under the protection of nitrogen gas and electromagnetic stirring, and monitored by thin layer chromatography. If there was a small amount of un-reacted 7-ethyl-10-hydroxyl camptothecin, suitable amounts of the solution A and triethylamine were additionally added until the reaction was completed. The reaction solution was added into ethyl acetate (100 mL), and the solid substances were removed by filtration. The filtrate was concentrated to 10 mL, and then isolated by column chromatography (the stationary phase was 230-400 mesh silica gel, and the eluent was a mixture of hexane and acetone), to obtain 7-ethyl-10-hydroxycamptothecin N-hexadecylamino R-(+)-6-hydroxy-2,5,7,8-tetramethylchroman-2-carboxamide-6-succinate (645 mg, yield 68.0%).

Example 6

Synthesis of camptothecin N-hexadecylamino R-(+)-6-hydroxy-2,5,7,8-tetramethylchroman-2-carboxamide-6-succinate The reaction scheme is shown as follows:

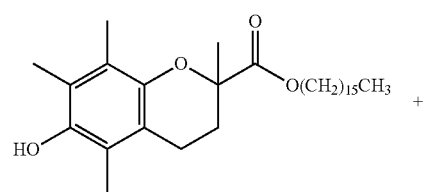

Procedure:

To a 50 mL reaction flask camptothecin (174 mg, 0.5 mmol), N-hexadecylamino R-(+)-6-hydroxy-2,5,7,8-tetramethylchroman-2-carboxamide-6-monosuccinate (287 mg, 0.5 mmol), 4-dimethylaminopyridine (147 mg, 1.2 mmol), 2-chloro-1-methylpyridinium iodide (153 mg, 0.6 mmol) and anhydrous N,N-dimethylacetamide (20 mL) were added under electromagnetic stirring. The reaction mixture was reacted for 4 h at room temperature under the protection of nitrogen gas and electromagnetic stirring. The reaction solution was added into ethyl acetate (100 mL), and the solid substances were removed by filtration. The filtrate was concentrated to 10 mL, and then isolated by column chromatography (the stationary phase was 230-400 mesh silica gel, and the eluent was a mixture of hexane and acetone), to obtain camptothecin N-hexadecylamino R-(+)-6-hydroxy-2,5,7,8-tetramethylchroman-2-carboxamide-6-succinate (316 mg, yield 70.0%).

Example 7

Synthesis of 7-ethyl-10-hydroxycamptothecin (±)-6-hydroxy-2,5,7,8-tetramethylchroman-2-carboxylic acid hexadecyl ester-6-oxyacetate 1) Synthesis of (±)-6-hydroxy-2,5,7,8-tetramethylchroman-2-carboxylic acid hexadecyl ester-6-oxyacetic acid ethyl ester The reaction scheme is shown as follows:

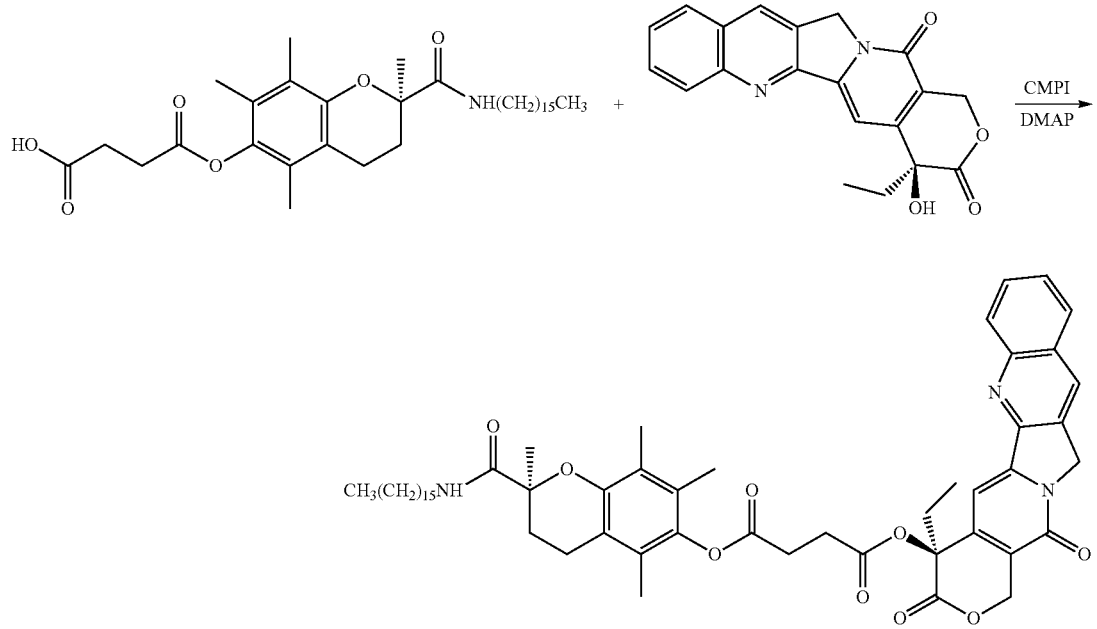

-continued

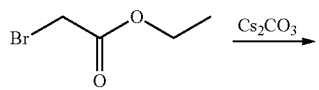

-continued

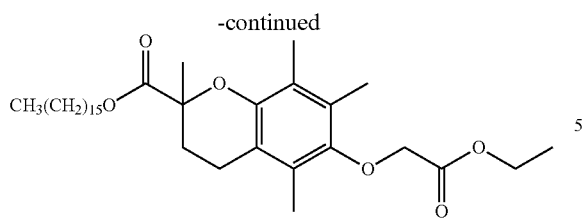

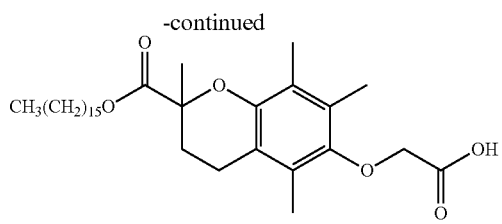

Procedure:

To a 50 mL reaction flask (±)-6-hydroxy-2,5,7,8-tetramethyl chroman-2-carboxylic acid hexadecyl ester (948 mg, 2 mmol), ethyl bromoacetate (501 mg, 3 mmol), cesium carbonate (652 mg, 2 mmol) and anhydrous N,N-dimethylformamide (20 mL) were added under electromagnetic stirring. The reaction mixture was reacted for 12 h at room temperature under the protection of nitrogen gas and electromagnetic stirring. N,N-dimethylformamide was removed by distillation under reduced pressure. To the resulting residue was added ethyl acetate (100 mL) and stirred. The solid substances were removed by filtration. The filtrate was concentrated to 10 mL, and then isolated by column chromatography (the stationary phase was 230-400 mesh silica gel, and the eluent was a mixture of hexane and acetone), to obtain (±)-6-hydroxy-2,5,7,8-tetramethylchroman-2-carboxylic acid hexadecyl ester-6-oxyacetic acid ethyl ester (864 mg, yield 77.0%).

2) Synthesis of (±)-6-hydroxy-2,5,7,8-tetramethylchroman-2-carboxylic acid hexadecyl ester-6-oxyacetic acid The reaction scheme is shown as follows:

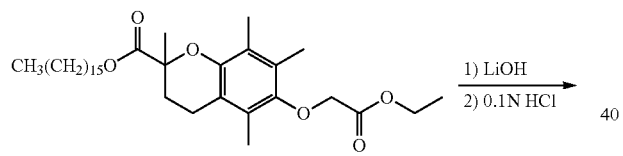

Procedure:

Under electromagnetic stirring, to a 50 mL reaction flask (±)-6-hydroxy-2,5,7,8-tetramethylchroman-2-carboxylic acid hexadecyl ester-6-oxyacetic acid ethyl ester (1122 mg, 2 mmol) and methanol (20 mL) were added, and then thereto lithium hydroxide (48 mg, 2 mmol) and water (5 mL) were added. The reaction mixture was reacted for 1 h at room temperature under the protection of nitrogen gas and electromagnetic stirring until (±)-6-hydroxy-2,5,7,8-tetramethylchroman-2-carboxylic acid hexadecyl ester-6-oxyacetic acid ethyl ester was completely reacted. Methanol was removed by distillation under reduced pressure. 0.1N HCl was dropwise added into the solution to pH of 3-4, and then freeze-dried. Ethyl acetate (10 mL) was added and stirred. The solid substances were removed by filtration. The resulting filtrate was isolated by column chromatography (the stationary phase was 230-400 mesh silica gel, and the eluent was a mixture of hexane and acetone), to obtain (±)-6-hydroxy-2,5,7,8-tetramethylchroman-2-carboxylic acid hexadecyl ester-6-oxyacetic acid (938 mg, yield 88%).

3) Synthesis of 7-ethyl-10-hydroxycamptothecin (±)-6-hydroxy-2,5,7,8-tetramethylchroman-2-carboxylic acid hexadecyl ester-6-oxyacetate The reaction scheme is shown as follows:

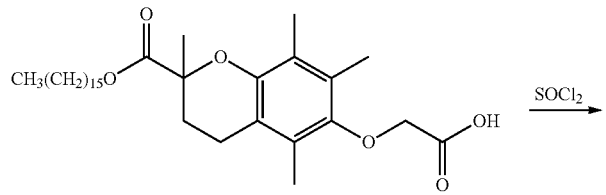

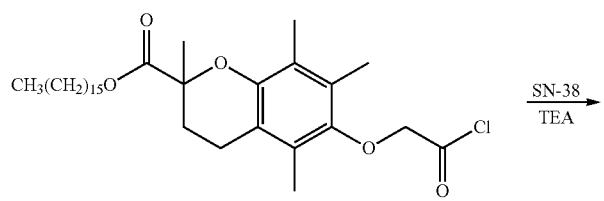

-continued

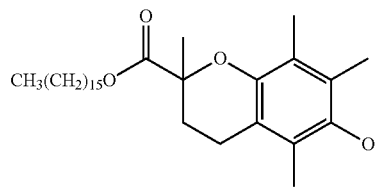

Procedure:

To a 50 mL reaction flask (±)-6-hydroxy-2,5,7,8-tetramethylchroman-2-carboxylic acid hexadecyl ester-6-oxyacetic acid (533 mg, 1 mmol), thionyl chloride (238 mg, 2 mmol), N,N-dimethylformamide (10 μL) and anhydrous toluene (20 mL) were added under electromagnetic stirring. The reaction mixture was reacted for 4 h at room temperature under the protection of nitrogen gas and electromagnetic stirring. Toluene and an excessive amount of thionyl chloride were removed by distillation under reduced pressure to obtain a viscous liquid, and thereto anhydrous chloroform (10 mL) was added to obtain solution A.

Under electromagnetic stirring, to a 50 mL reaction flask 7-ethyl-10-hydroxycamptothecin (196 mg, 0.5 mmol), anhydrous triethylamine (61 mg, 0.6 mmol) and anhydrous N,N-dimethylacetamide (20 mL) were added, and then thereto the solution A (6 mL) was slowly added. The reaction mixture was reacted for 4 h at room temperature under the protection of nitrogen gas and electromagnetic stirring, and monitored by thin layer chromatography. If there was a small amount of un-reacted 7-ethyl-10-hydroxycamptothecin, suitable amounts of the solution A and triethylamine were additionally added until the reaction was completed. The reaction solution was added into ethyl acetate (100 mL), and the solid substances were removed by filtration. The filtrate was concentrated to 10 mL, and then isolated by column chromatography (the stationary phase was 230-400 mesh silica gel, and the eluent was a mixture of hexane and actone), to obtain 7-ethyl-10-hydroxycamptothecin (±)-6-hydroxy-2,5,7,8-tetramethylchroman-2-carboxylic acid hexadecyl ester-6-oxyacetate (259 mg, yield 57.0%).

Example 8

Synthesis of camptothecin (±)-6-hydroxy-2,5,7,8-tetramethylchroman-2-carboxylic acid hexadecyl ester-6-oxyacetate The reaction scheme is shown as follows:

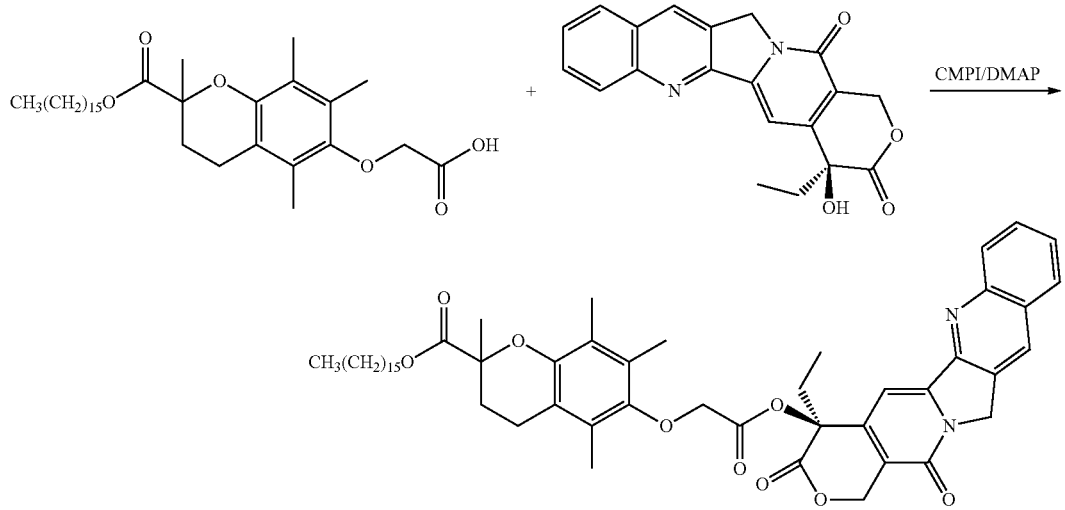

Procedure:

To a 50 mL reaction flask camptothecin (348 mg, 1 mmol), 4-dimethylaminopyridine (244 mg, 2 mmol), 2-chloro-1-methylpyridinium iodide (255 mg, mmol), (±)-6-hydroxy-2,5,7, 8-tetramethylchroman-2-carboxylic acid hexadecyl ester-6-oxyacetic acid (533 mg, 1 mmol) and anhydrous N,N-dimethylacetamide (20 mL) were added under electromagnetic stirring. The reaction mixture was reacted for 4 h at room temperature under the protection of nitrogen gas and electromagnetic stirring. The solid substances were removed by filtration, and the filtrate was concentrated to 10 mL by a rotary evaporator, and then isolated by column chromatography (the stationary phase was 230-400 mesh silica gel, and the eluent was a mixture of hexane and acetone), to obtain (±)-6-hydroxy-2,5,7,8-tetramethylchroman-2-carboxylic acid hexadecyl ester-6-oxyacetate (630 mg, yield 73.0%).

Example 9

Synthesis of camptothecin (±)-6-hydroxy-2,5,7,8-tetramethylchroman-2-carboxylic acid hexadecyl ester-6-methylphosphonyl ester The reaction scheme is shown as follows:

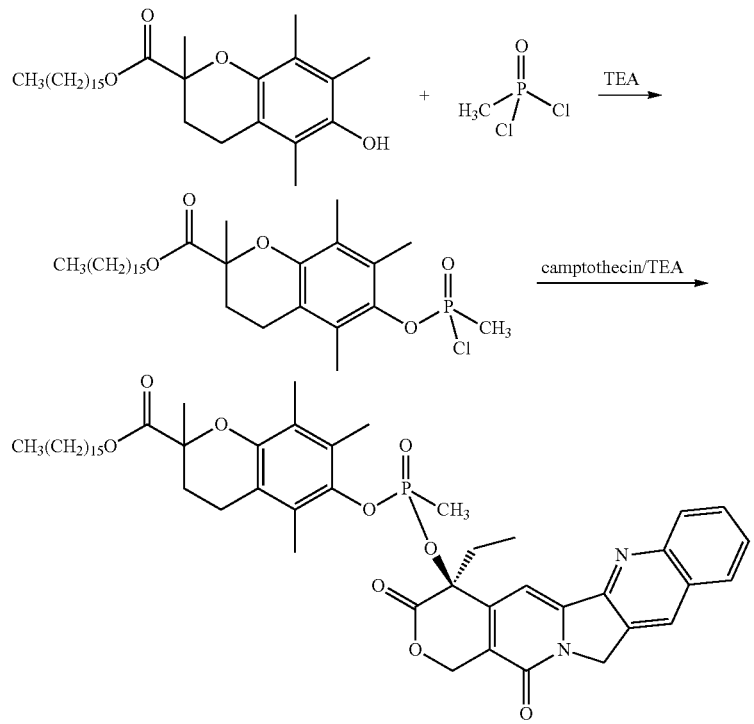

Procedure:

Under electromagnetic stirring, to a 100 mL reaction flask methylphosphonyl dichloride (293 mg, 2.2 mmol) and anhydrous diethyl ether (20 mL), and then a mixture of (±)-6-hydroxy-2,5,7,8-tetramethylchroman-2-carboxylic acid hexadecyl ester (949 mg, 2 mmol), triethylamine (202 mg, 2 mmol) were added, and anhydrous diethyl ether (20 mL) was slowly dropwise added. The reaction mixture was reacted for 8 h at room temperature under the protection of nitrogen and electromagnetic stirring. Diethyl ether was removed by distillation under reduced pressure, and the residue was dried under vacuum to obtain (±)-6-hydroxy-2,5,7,8-tetramethylchroman-2-carboxylic acid hexadecyl ester-6-methylphosphonyl chloride ester (1096 mg, yield 96.0%).

To a 50 mL reaction flask camptothecin (348 mg, 1 mmol), triethylamine (111 mg, 1.1 mmol), (±)-6-hydroxy-2,5,7,8-tetramethylchroman-2-carboxylic acid hexadecyl ester-6-methylphosphonyl chloride ester (628 mg, 1.1 mmol) and anhydrous N,N-dimethylacetamide (20 mL) were added under electromagnetic stirring. The reaction mixture was reacted for 4 h at room temperature under the protection of nitrogen gas and electromagnetic stirring. The solid substances were removed by filtration, and the filtrate was concentrated to 10 mL by a rotary evaporator, and then isolated by column chromatography (the stationary phase was 230-400 mesh silica gel, and the eluent was a mixture of hexane and acetone), to obtain camptothecin (±)-6-hydroxy-2,5,7,8-tetramethylchroman-2-carboxylic acid hexadecyl ester-6-methylphosphonyl ester (732 mg, yield 83.0%).

Example 10

Preparations of Fat-Soluble Anti-Cancer Pharmaceutical Compounds, Including Emulsion and Micelle Preparations This example includes emulsion and micelle preparations of fat-soluble anti-cancer pharmaceutical compounds. The emulsion and micelle preparations may comprise the fat-soluble anti-cancer pharmaceutical compounds of the present invention. The content of each component in the preparations is calculated as weight percentage of the preparations. The pharmaceutical compounds in the preparations may be replaced with other fat-soluble anti-cancer pharmaceutical compounds of the present invention.

A: Emulsion of 7-ethyl-10-hydroxycamptothecin R-(+)-6-hydroxy-2,5,7,8-tetramethylchroman-2-carboxylic acid hexadecyl ester-6-succinate 7-ethyl-10-hydroxycamptothecin R-(+)-6-hydroxy-2,5,7,8-tetramethyl chroman-2-carboxylic acid hexadecyl ester-6-succinate (MXL-003) was dissolved in a mixture of soybean oil, D-α-tocopherol polyethylene glycol 1000 succinate (TPGS) and polyethylene glycol PEG (200). Deionized water (DI water) was then added, and subsequently the mixture was stirred and ultrasonically emulsified. The resulting emulsion had the following composition:

| | |
|---|---|
| MXL-003 | 1% |
| Soybean oil | 10% |
| TPGS | 5% |
| PEG(200) | 3% |
| DI water | balanced to 100% |

The formulated emulsion preparation was filtered by a filter having a pore size of 0.2 micron, and then filled into a sterile glass vial.

B: Emulsion of 7-ethyl-10-hydroxycamptothecin R-(+)-6-hydroxy-2,5,7,8-tetramethylchroman-2-carboxylic acid dodecyl ester-6-succinate 7-ethyl-10-hydroxycamptothecin R-(+)-6-hydroxy-2,5,7,8-tetramethyl chroman-2-carboxylic acid dodecyl ester-6-succinate (MXL-002) was dissolved in a mixture of D-α-tocopherol acetate, D-α-tocopherol polyethylene glycol 1000 succinate (TPGS) and polyethylene glycol PEG (200). Physiological saline was then added, and subsequently the mixture was stirred and ultrasonically emulsified. The resulting emulsion had the following composition:

| | |
|---|---|
| MXL-002 | 0.1% |
| D-α-tocopherol acetate | 6% |
| TPGS | 4% |
| PEG(200) | 10% |
| Physiological saline | balanced to 100% |

The formulated emulsion preparation was filtered by a filter having a pore size of 0.2 micron, and then filled into a sterile glass vial.

C: Micelle solution of 7-ethyl-10-hydroxycamptothecin R-(+)-6-hydroxy-2,5,7,8-tetramethylchroman-2-carboxylic acid hexadecyl ester-6-succinate 7-ethyl-10-hydroxycamptothecin R-(+)-6-hydroxy-2,5,7,8-tetramethyl chroman-2-carboxylic acid hexadecyl ester-6-succinate (MXL-003) was dissolved in a mixture of Tween 80, ethanol and polyethylene glycol PEG (200) to obtain a transparent liquid. Deionized water (DI water) was then added, and subsequently the mixture was stirred. The resulting micelle solution had the following composition:

| | |
|---|---|
| MXL-003 | 0.05% |
| Tween 80 | 5% |
| Ethanol | 5% |
| PEG200 | 5% |
| DI water | balanced to 100% |

The formulated micelle preparation was filtered by a filter having a pore size of 0.2 micron, and then filled into a sterile glass vial.

D: Micelle solution of 7-ethyl-10-hydroxycamptothecin R-(+)-6-hydroxy-2,5,7,8-tetramethylchroman-2-carboxylic acid dodecyl ester-6-succinate 7-ethyl-10-hydroxycamptothecin R-(+)-6-hydroxy-2,5,7,8-tetramethylchroman-2-carboxylic acid dodecyl ester-6-succinate (MXL-002) was dissolved in a mixture of D-α-tocopherol polyethylene glycol 1000 succinate (TPGS), ethanol and polyethylene glycol PEG (200) to obtain a transparent liquid. Physiological saline was then added, and subsequently the mixture was stirred. The resulting micelle solution had the following composition:

| | |
|---|---|
| MXL-002 | 1.0% |
| TPGS | 4% |
| Ethanol | 10% |
| PEG200 | 5% |
| Physiological saline | balanced to 100% |

The formulated emulsion preparation was filtered by a filter having a pore size of 0.2 micron, and then filled into a sterile glass vial.

Example 11

In Vitro Cytotoxicity Test of Fat-Soluble Anti-Cancer Pharmaceutical Compounds In this example, GI50 values (the concentration of a drug that inhibits the growth of cancer cells by 50%) of the novel anti-cancer pharmaceutical compounds of the present invention on the inhibition of human ovarian cancer cells (A2780s), colon cancer cells (HT-29), liver cancer HePG$_2$ cells and lung cancer cells (A549) were determined by MTT assay, and further compared with that of anti-cancer drug irinotecan to evaluate in vitro cytotoxicity of the pharmaceutical compounds of the present invention.

GI50 values are shown in table 1. Other anti-cancer pharmaceutical compounds of the present invention have the similar results and also have significantly reduced GI50 values. The experimental results indicate that the anti-cancer pharmaceutical compounds of the present invention have significant effect of proliferation inhibition on human ovarian cancer cells (A2780s), colon cancer cells (HT-29), liver cancer HePG$_2$ cells and lung cancer cells (A549). Moreover, the proliferation inhibition effect of the pharmaceutical compounds on these cells would be enhanced with the increase of the concentration thereof, which exhibits an apparent dose-dependent effect. The anti-cancer pharmaceutical compounds of the present invention has more significant inhibiting effect on human ovarian cancer cells, colon cancer cells, live cancer cells and lung cancer cells than the positive effective drug irinotecan having the same concentration. The anti-cancer pharmaceutical compounds of the present invention have inhibiting effect on the proliferation of human ovarian cancer cells (A2780s), colon cancer cells (HT-29), liver cancer HePG$_2$ cells and lung cancer cells (A549), and accordingly belong to a class of potential pharmaceutical compounds against human ovarian cancer, colon cancer, liver cancer and lung cancer.

MTT assay: Cells in logarithmic growth phase were seeded in 96-well culture plate at 100 µL/well and a cell density of $10^5$/mL. After the cells were incubated for 18 h, the medium was replaced, and thereto the test compound samples with different concentrations were then added at 150 µL/well. The blank group was the wells to which only a RPMI 1640 culture medium comprising 10% fetal bovine serum was added without the addition of cells (for zero setting). The negative control group was the wells to which the equal volume of RPMI 1640 culture medium comprising 10% fetal bovine serum was added and the positive control group was the wells to which the equal volume of 13 µg/ml positive drug was added. Each group had three wells. After the cells were incubated for 72 h, MTT (5 mg/mL) solution was added at 15 µL/well, and the cells were further incubated for 4 h. The supernatant was discarded, and DMSO was added at 150 µL/well. The mixture was shaken and blended for 10 min. After the crystal was completely dissolved, the absorbance (D) value of each well was detected on microplate reader at a wavelength of 490 nm. The cell growth inhibition rate was calculated according to the following equation:

Cell growth inhibition rate=(1−average $D$ value of test group/average $D$ value of control group)×100%.

TABLE 1

Comparision of GI50s of novel anti-cancer drugs vs anti-cancer drug-irinotecan

| Novel anti-cancer drug | MXL-001 | MXL-002 | MXL-003 | Irinotecan |
|---|---|---|---|---|
| Ovarian cancer cell (A2780s) | 40.9 nM | 17.8 nM | 16.9 nM | 19.30 µM |
| Colon cancer cells (HT-29) | NP | NP | 0.045 µM | 15.19 µM |
| Live cancer cells (HePG$_2$) | NP | NP | 0.164 µM | 9.442 µM |
| Lung cancer cells (A549) | 4.6 µM | 2.1 µM | 0.169 µM | 58.07 nM |

NP: not detected.
MXL-001: 7-ethyl-10-hydroxycamptothecin R-(+)-6-hydroxy-2,5,7,8- tetramethylchroman-2-carboxylic acid n-hexyl ester-6-succinate.
MXL-002: 7-ethyl-10-hydroxycamptothecin R-(+)-6-hydroxy-2,5,7,8- tetramethylchroman-2-carboxylic acid dodecyl ester-6-succinate.
MXL-003: 7-ethyl-10-hydroxycamptothecin R-(+)-6-hydroxy-2,5,7,8- tetramethylchroman-2-carboxylic acid hexadecyl ester-6-succinate.

The invention claimed is:

1. A trolox derivative-modified pharmaceutical compound, having a structure as represented by formula I:

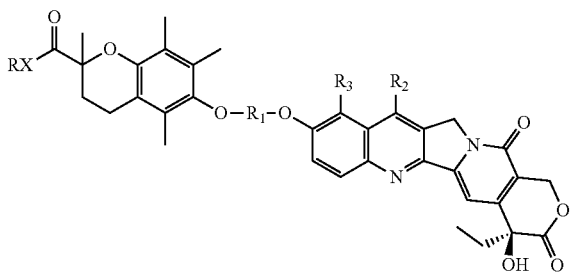

I wherein:
R is a lipophilic group selected from the group consisting of
a) unsubstituted linear alkyl;
b) unsubstituted cycloalkyl; and
c) unsubstituted branched alkyl;
R$_1$ is a linking group selected from the group consisting of
a) —(C=O)(CH$_2$)$_n$(C=O)—, wherein n=2; and
b) —(CH$_2$)$_n$(C=O)—, wherein n=1;
X is —O—, —NH— or —NR'—, wherein R' is C$_1$-C$_6$ alkyl;
R$_2$ is H or C$_1$-C$_6$ alkyl; and
R$_3$ is H.

2. The trolox derivative-modified pharmaceutical compound of claim 1, wherein trolox in the pharmaceutical compound is an optical isomer thereof.

3. A method for treating human ovarian cancer, colon cancer, liver cancer, and lung cancer, comprising administering a therapeutically effective amount of the trolox derivative-modified pharmaceutical compound of claim 1 to a subject in need thereof.

4. The method of claim 3, wherein the trolox derivative-modified pharmaceutical compound has a structure represented by formula I:

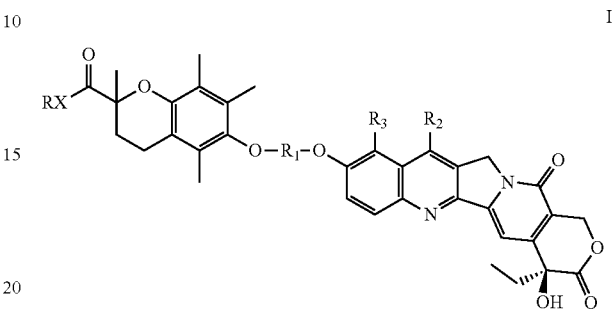

I wherein
R is —(CH$_2$)$_{15}$CH$_3$;
R$_1$ is —(C=O)(CH$_2$)$_2$(C=O)—;
X is —O—;
R$_2$ is —CH$_2$CH$_3$; and
R$_3$ is H.

5. The trolox derivative-modified pharmaceutical compound of claim 1, wherein it has a structure represented by formula I

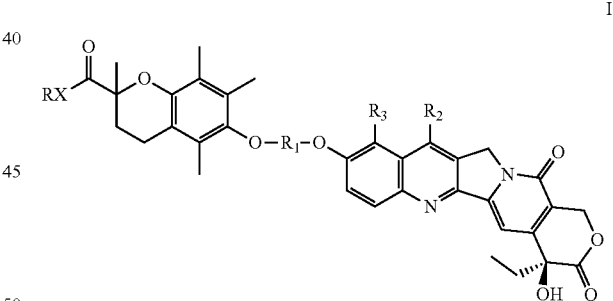

I wherein:
R$_1$ is an unsubstituted linear alkyl;
R$_1$ is a linking group selected from the group consisting of
a) —(C=O)(CH$_2$)$_n$(C=O)—, wherein n=2; and
b) —(CH$_2$)$_n$(C=O)—, wherein n=1;
X is —O—;
R$_2$ is H or C$_1$-C$_6$ alkyl; and
R$_3$ is H.

6. The trolox derivative-modified pharmaceutical compound of claim 5, wherein it has a structure represented by formula I

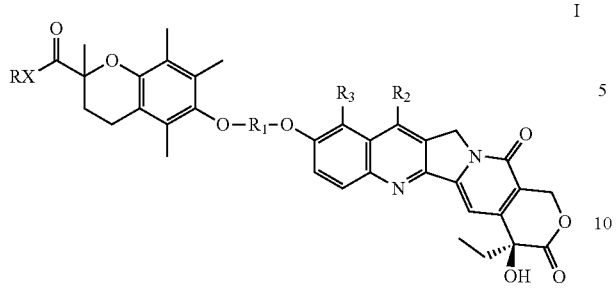
I
wherein:
R is an unsubstituted linear alkyl;
$R_1$ is —(C=O)(CH$_2$)$_n$(C=O)—, wherein n=2;
X is —O—;
$R_2$ is —CH$_2$CH$_3$; and
$R_3$ is H.
7. The trolox derivative-modified pharmaceutical compound of claim 6, wherein it has a structure represented by formula I
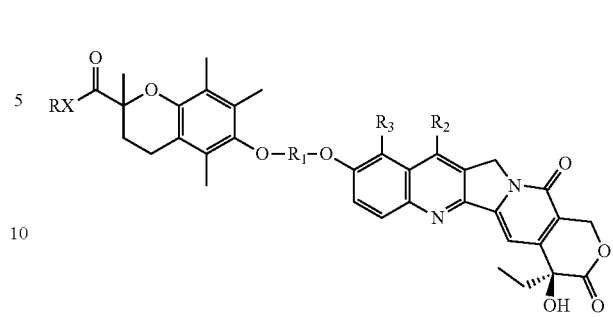
I
wherein:
R is —(CH$_2$)$_{15}$CH$_3$;
$R_1$ is —(C=O)(CH$_2$)$_n$(C=O)—, wherein n=2;
X is —O—;
$R_2$ is —CH$_2$CH$_3$;
$R_3$ is H.
* * * * *